US008653302B2

(12) United States Patent
Umemoto

(10) Patent No.: US 8,653,302 B2
(45) Date of Patent: Feb. 18, 2014

(54) PROCESSES FOR PREPARING POLY(PENTAFLUOROSULFANYL)AROMATIC COMPOUNDS

(75) Inventor: Teruo Umemoto, Westminster, CO (US)

(73) Assignee: UBE Industries, Ltd., Yamaguchi (JP)

(*) Notice: Subject to any disclaimer, the term of this patent is extended or adjusted under 35 U.S.C. 154(b) by 0 days.

(21) Appl. No.: 13/119,367

(22) PCT Filed: Sep. 21, 2009

(86) PCT No.: PCT/US2009/057714
§ 371 (c)(1),
(2), (4) Date: Mar. 16, 2011

(87) PCT Pub. No.: WO2010/033930
PCT Pub. Date: Mar. 25, 2010

(65) Prior Publication Data
US 2011/0166392 A1 Jul. 7, 2011

Related U.S. Application Data

(60) Provisional application No. 61/098,975, filed on Sep. 22, 2008, provisional application No. 61/143,564, filed on Jan. 9, 2009.

(51) Int. Cl.
C07C 323/00 (2006.01)

(52) U.S. Cl.
USPC .............................. 562/824; 562/821; 568/74

(58) Field of Classification Search
USPC .............................. 568/74; 562/824, 527, 821
See application file for complete search history.

(56) References Cited

U.S. PATENT DOCUMENTS

| 3,054,661 | A | 9/1962 | Muetterties |
| 3,919,204 | A | 11/1975 | Boswell, Jr. et al. |
| 4,147,733 | A | 4/1979 | Fiske et al. |
| 4,316,906 | A | 2/1982 | Ondetti et al. |
| 5,055,223 | A | 10/1991 | Reiffenrath et al. |
| 5,093,432 | A | 3/1992 | Bierschenk et al. |
| 5,395,916 | A | 3/1995 | Mochizuki et al. |
| 5,455,373 | A | 10/1995 | Kawa |
| 5,691,081 | A | 11/1997 | Krause et al. |
| 5,741,935 | A | 4/1998 | Bowden et al. |
| 5,789,580 | A | 8/1998 | Chambers et al. |
| 5,824,827 | A | 10/1998 | Bildinov et al. |
| 6,222,064 | B1 | 4/2001 | Lal et al. |
| 6,737,193 | B2 | 5/2004 | Umemoto |
| 6,958,415 | B2 | 10/2005 | Lal et al. |
| 7,015,176 | B2 | 3/2006 | Bailey, III et al. |
| 7,045,360 | B2 | 5/2006 | Shair et al. |
| 7,087,681 | B2 | 8/2006 | Umemoto |
| 7,265,247 | B1 | 9/2007 | Umemoto et al. |
| 7,279,584 | B2 | 10/2007 | Tomisawa et al. |
| 7,351,863 | B2 | 4/2008 | Hara et al. |
| 7,381,846 | B2 | 6/2008 | Umemoto et al. |
| 7,501,543 | B2 | 3/2009 | Umemoto et al. |
| 7,592,491 | B2 | 9/2009 | Umemoto |
| 7,820,864 | B2 | 10/2010 | Umemoto et al. |
| 7,851,646 | B2 | 12/2010 | Umemoto |
| 7,919,635 | B2 | 4/2011 | Umemoto |
| 8,030,516 | B2 | 10/2011 | Umemoto et al. |
| 8,203,003 | B2 | 6/2012 | Umemoto et al. |
| 2001/0021792 | A1 | 9/2001 | Nakada et al. |
| 2001/0049457 | A1 | 12/2001 | Stephens |
| 2003/0060669 | A1 | 3/2003 | Shibata et al. |
| 2004/0022720 | A1 | 2/2004 | Low et al. |
| 2004/0106827 | A1 | 6/2004 | Dolbier et al. |
| 2004/0209854 | A1 | 10/2004 | Barkalow et al. |
| 2004/0249209 | A1* | 12/2004 | Bailey et al. .................. 562/824 |
| 2005/0012072 | A1 | 1/2005 | Bailey, III et al. |
| 2005/0148652 | A1 | 7/2005 | Kleemann et al. |
| 2006/0014972 | A1 | 1/2006 | Hara et al. |
| 2009/0105502 | A1 | 4/2009 | Umemoto et al. |
| 2009/0203924 | A1 | 8/2009 | Umemoto et al. |
| 2009/0287024 | A1 | 11/2009 | Umemoto et al. |
| 2010/0029992 | A1 | 2/2010 | Umemoto et al. |
| 2010/0076215 | A9 | 3/2010 | Umemoto et al. |
| 2010/0152463 | A1 | 6/2010 | Umemoto et al. |
| 2010/0174096 | A1 | 7/2010 | Umemoto et al. |
| 2010/0234605 | A1 | 9/2010 | Umemoto et al. |
| 2011/0004022 | A1 | 1/2011 | Umemoto |
| 2011/0009672 | A1 | 1/2011 | Umemoto |
| 2011/0160488 | A1 | 6/2011 | Umemoto |
| 2011/0190511 | A1 | 8/2011 | Umemoto et al. |
| 2011/0275833 | A1 | 11/2011 | Umemoto et al. |
| 2011/0301382 | A1 | 12/2011 | Umemoto et al. |
| 2011/0306798 | A1 | 12/2011 | Umemoto |
| 2012/0157716 | A1 | 6/2012 | Umemoto et al. |

FOREIGN PATENT DOCUMENTS

| DE | 19748109 A1 | 5/1999 |
| EP | 0361907 A2 | 4/1990 |
| EP | 1484318 A1 | 12/2004 |

(Continued)

OTHER PUBLICATIONS

Ou et al, Canadian Journal of Chemistry, 75; 1878-1884 (1997).*
Andrieux et al. (1990) "Outer-sphere and inner-sphere processes in organic chemistry. Reaction of trifluoromethyl bromide with electrochemically generated aromatic anion radicals and sulfur dioxide anion radicals" J. Am. Chem. Soc. 112(2): 786-791.
Bégué and Bonnet-Delpon (2006) "Recent Advances (1995-2005) in Fluorinated Pharmaceuticals Based on Natural Products" Journal of Fluorine Chemistry 127:992-1012+A3.
Bowden et al. (2000) "A New Method for the Synthesis of Aromatic Sulfurpentafluorides and Studies of the Stability of the Sulfurpentafluoride Group in Common Synthetic Transformation" Tetrahedron 56:3399-3408.
Bunnelle et al. (1990) "Difluorination of Esters. Preparation of α, α-Difluoro Ethers" J. Org. Chem. 55(2):768-770.
Calamari and Trask (1979) "Laboratory Explosions" Chemical & Engineering News, 57(19):4.

(Continued)

Primary Examiner — Johann R Richter
Assistant Examiner — Pancham Bakshi
(74) Attorney, Agent, or Firm — Swanson & Bratschun, LLC

(57) ABSTRACT

Novel processes for preparing poly(pentafluorosulfanyl)aromatic compounds are disclosed. Processes include reacting an aryl sulfur compound with a halogen and a fluoro salt to form a poly(halotetrafluorosulfanyl)aromatic compound. The poly(halotetrafluorosulfanyl)aromatic compound is reacted with a fluoride source to form a target poly(pentafluorosulfanyl)aromatic compound.

12 Claims, No Drawings

(56) References Cited

FOREIGN PATENT DOCUMENTS

| | | |
|---|---|---|
| GB | 2276379 | 9/1994 |
| JP | H02-154266 A | 6/1990 |
| JP | 2003-077861 | 4/1991 |
| JP | H07-292050 A | 11/1995 |
| JP | H09-500893 A | 1/1997 |
| JP | 2000-38370 A | 8/2000 |
| JP | 2004-359687 A | 12/2004 |
| JP | 4531852 | 6/2010 |
| WO | WO 94/21606 | 9/1994 |
| WO | WO 01/27076 | 4/2001 |
| WO | WO 03/002553 | 1/2003 |
| WO | WO 2004/011422 | 2/2004 |
| WO | WO 2004/050676 | 6/2004 |
| WO | WO 2008/013550 | 1/2008 |
| WO | WO 2008/014345 | 1/2008 |
| WO | WO 2008/118787 | 10/2008 |
| WO | WO 2009/076345 | 6/2009 |
| WO | WO 2009/114409 | 9/2009 |
| WO | WO 2010/014665 | 2/2010 |
| WO | WO 2010/022001 | 2/2010 |
| WO | WO 2010/033930 | 3/2010 |
| WO | WO 2010/081014 | 7/2010 |

OTHER PUBLICATIONS

Cava and Levinson (1985) "Thionation Reactions of Lawesson's Reagents" Tetrahedron 41(22):5061-5087.

Chambers et al. (1996) "Elemental Fluorine. Part 5.1,2 Reactions of 1,3-Dithiolanes and Thioglycosides With Fluorine-Iodine Mixtures" J. Chem. Soc. Perkin Trans. 1 1941-1944.

Cochran (Mar. 19, 1979) "Laboratory Explosions" Chemical & Engineering News 57(19):4.

Davis et al (1999) "Efficient Asymmetric Synthesis of β-Fluoro α-Amino Acids" J. Org. Chem. 64:6931-6934.

Des Marteau (1995) "Novel perfluorinated ionomers and ionenes" J. Fluorine Chem. 72(2): 203-208.

Feiring (1979) "Chemistry in Hydrogen Fluoride. 7. A Novel Synthesis of Aryl Trifluoromethyl Ethers" J. Org. Chem. 44(16):2907-2910.

Folest et al. (1988) "Electrochemical Synthesis of Trifluoromethane Sulfinic Acid Salt From CF3Br and SO2" Synthetic Communications 18(13): 1491-1494.

Furuya et al. (2005) "Synthesis of gem-difluorides From Aldehydes Using DFMBA" Journal of Fluorine Chemistry 126:721-725.

Hasek et al. (1960) "The Chemistry of Sulfur Tetrafluoride. II. The Fluorination of Organic Carbonyl Compounds" Journal of American Chem. Soc. 82(3):543-551.

Hayashi et al. (2002) "2,2-Difluoro-1,3-dimethylimidazolidine (DFI). A New Fluorinating Agent" Chem. Commun. 1618-1619.

Henne and Nager (1951) "Trifluoropropyne" J. Am. Chem. Soc. 73(3):1042-1043.

Hollitzer and Sartori (1987) "The electrochemical perfluorination (ECPF) of propanesulfonyl fluorides. I: Preparation and ECPF of 1-propanesulfonyl fluoride and 1,3-propanedisulfonyl difluoride" J. Fluorine Chem. 35(2): 329-341.

Hoover and Coffman (1964) "Synthesis and Chemistry of Ethynylsulfur Pentafluoride" Journal of Organic Chem. 29:3567-3570.

Howe-Grant (1995) "Sulfur Hexafluoride" Fluorine Chemistry: A Comprehensive Treatment, John Wiley & Sons, Inc., New York (ISBN: 0-471-12031-6) pp. 188-195.

Hu and DesMarteau (1993) "Synthesis of Perhaloalkanesulfonyl Halides and Their Sulfonimide Derivatives" Inorg. Chem. 32:5007-5010.

Kirsch and Bremer (2000) "Nematic Liquid Crystals for Active Matrix Displays: Molecular Design and Synthesis" Angew. Chem. Int. Ed. 39:4216-4235.

Kirsch and Hahn (2005) "Liquid Crystals Based on Hypervalent Sulfur Fluorides: Exploring the Steric Effects of ortho-Fluorine Substituents" Eur. J. of Org. Chem. 3095-3100.

Kobayashi et al.(2004) "Deoxyfluorination of alcohols using N,N-diethyl-α, α-difluoro-(m-methylbenzyl)amine" Tetrahedron 60:6923-6930.

Kuroboshi et al. (1992) "Oxidative Desulfurization-Fluorination of Xanthates. A Convenient Synthesis of Trifluoromethyl Ethers and Difluoro(methylthio)methyl Ethers" Tetrahedron 33(29): 4173-4176.

Kuroboshi and Hiyama (1991) "A Facile Synthesis of Difluoromethylene Compounds by Oxidative Fluorodesulfurization of Dithioacetals Using Tetrabutylammonium Dihydrogentrifluoride and N-Halo Compounds" Synlett 909-910.

Kuroboshi and Hiyama (1992) "A Facile Synthesis of Trifluoromethylamines by Oxidative Desulfurization-Fluorination of Dithiocarbamates" Tetrahedron 33(29):4177-4178.

Kuroboshi and Hiyama (1992) "Oxidative Desulfurization-Fluorination of Methyl Arenedithiocarboxylates. A Convenient Synthesis of Trifluoromethylated Aromatic Compounds" Chemistry Letters 827-830.

Kuroboshi and Hiyama (1994) "A Convenient Synthesis of Perfluoroalkylated Amines by Oxidative Desulfurization-Fluorination" Tetrahedron 35(23):3983-3984.

Kuroboshi and Hiyama (1994) "A Facile Synthesis of α, α-Difluoroalkyl Ethers and Carbonyl Fluoride Acetals by Oxidative Desulfurization-Fluorination" Synlett 251-252.

Lal et al. (1999) "Bis(2-methoxyethyl)aminosulfur trifluoride: a new broad-spectrum deoxofluorinating agent with enhanced thermal stability" Chem. Commun.215-216.

Lal et al. (2000) "Fluorination of Thiocarbonyl Compounds with Bis(2-methoxyethyl)aminosulfur Trifluoride (Deoxo-Fluor Reagent): A Facile Synthesis of gem-Difluorides" J. Org. Chem. 65:4830-4832.

Lee et al. (1989) "One Pot Phase Transfer Synthesis of O-Alkyl, S-Methyl Dithiocarbonates (Xanthates)" Synthetic Communications 19(3&4):547-552.

Ma and Cahard (2007) "Strategies for Nucleophilic, Electrophilic, and Radical Trifluoromethylations" Journal of Fluorine Chemistry 128:975-996.

Methods of Organic Chemistry (Houben-Weyl), Work Bench Edition vol. E 10A, Organo-Fluorine Compounds, Gorge Thieme Verlag Stuttgart, New York, 2000 p. 194-201.

Middleton (1975) "New Fluorinating Reagents. Dialkylaminosulfur Fluorides" Journal of Organic Chem. 40(5):574-578.

Moss et al. (1995) "Glossary of Class Names of Organic Compounds and Reactive Intermediates Based on Structure" Pure & Appl. Chem, 67(8/9):1307-1375.

Motherwell and Wilkinson (1991) "Observations on the Reaction of Dithioketals with Para-Iodotoluene Difluoride: A Novel Route to Gem-Difluoro Compounds" Synlett 191-192.

Notice of Allowance mailed Jul. 26, 2011 with respect to U.S. Appl. No. 12/253,030.

Notice of Allowance mailed Jun. 21, 2011 with respect to U.S. Appl. No. 12/253,030.

Notice of Allowance mailed Dec. 7, 2010 with respect to U.S. Appl. No. 12/367,171.

Notice of Allowance mailed Oct. 28, 2010 with respect to U.S. Appl. No. 12/367,171.

Notice of Allowance mailed Jun. 23, 2010 with respect to U.S. Appl. No. 12/473,109.

Notice of Allowance mailed Aug. 6, 2010 with respect to U.S. Appl. No. 12/473,129.

Notice of Allowance mailed Oct. 31, 2008 with respect to U.S. Appl. No. 12/106,460.

Notice of Allowance mailed Apr. 29, 2009 with respect to U.S. Appl. No. 12/053,775.

Office Action mailed Aug. 4, 2011 with respect to U.S. Appl. No. 12/647,973.

Office Action mailed Jun. 1, 2011 with respect to U.S. Appl. No. 12/633,414.

Office Action mailed Jan. 21, 2011 with respect to U.S. Appl. No. 12/305,868.

Office Action mailed Sep. 13, 2010 with respect to U.S. Appl. No. 12/633,414.

(56) References Cited

OTHER PUBLICATIONS

Office Action mailed Mar. 2, 2010 with respect to U.S. Appl. No. 12/473,129.
Office Action mailed Jan. 7, 2010 with respect to U.S. Appl. No. 12/473,109.
Office Action mailed Oct. 22, 2009 with respect to U.S. Appl. No. 12/367,171.
Office Action mailed Nov. 20, 2007 with respect to U.S. Patent No. 7,381,846.
Office Action mailed Dec. 3, 2008 with respect to U.S. Patent No. 7,592,491.
Oae, Shigeru (1977) "Sulfoxides and Sulfilimines" Organic Chemistry of Sulfur, Plenum Press, NY and London, Chapters 8 and 10, pp. 384-589.
Oae, Shigeru (1977) "Sulfoxides and Sulfilimines" Organic Chemistry of Sulfur, Plenum Press, NY and London, Chapter 10, Section 10.3.7, pp. 572-577.
Olah et al. (1974) "Synthetic Methods and Reactions. I. Selenium Tetrafluoride and Its Pyridine Complex. Convenient Fluorinating Agents for Fluorination of Ketones, Aldehydes, Amides, Alcohols, Carboxylic Acids, and Anhydrides" Journal of American Chem. Soc. 96(3):925-927.
Ou et al. (1997) "Oxidative Addition and Isomerization Reactions. The Synthesis of cis- and trans-ArSF4Cl and cis- and trans-PHTeF4Cl" Can. Journal of Chem. 75:1878-1884.
Ou and Janzen (2000) "Oxidative Fluorination of S, Se and Te Compounds" Journal of Fluorine Chem. 101:279-283.
Pashinnik et al. (2003) "A New Method for the Synthesis of Organosulfur Trifluorides" Synthetic Communications 33(14):2505-2509.
Patai and Rappoport (1994) "Synthesis of Sulphoxides" The Synthesis of Sulphones, Sulphoxides and Cyclic Sulphides, John Wiley & Sons, An Interscience Publication, Chapter 3, pp. 109-158.
Petrov et al. (2001) "1,1,2,2-Tetrafluoroethyl-N,N-dimethylamine: A New Selective Fluorinating Agent" Journal of Fluorine Chemistry 109:25-31.
Petrov et al. (2004) "Quadricyclane—thermal cycloaddition to polyfluorinated carbonyl compounds: A simple synthesis of polyfluorinated 3-oxatricyclo[4.2.1.02,5]non-7-enes" Journal of Fluorine Chem. 125(10): 1543-1552.
Prakash et al. (1993) "Simplified Preparation of α,α-Difluorodiphenlmethanes From Benzophenone 1,3-Dithiolanes With Sulfuryl Choride and Pyridinium Polyhydrogen Fluoride" Synlett 691-693.
Qiu and Burton (1993) "A useful synthesis of ω-iodoperfluoroalkanesulfonyl fluorides and perfluoroalkane-α,ω-bis-sulfonyl fluorides" J. Fluorine Chem. 60(1): 93-100.
Reddy et al. (2005) "gem-Difluorination of 2,2-Diaryl-1,3-dithiolanes by Selectfluor® and Pyridinium Polyhydrogen Fluoride" Chem. Commun. 654-656.
Rozen and Mishani (1993) "Conversion of Esters to α, α-Difluoro Ethers Using Bromine Trifluoride" J. Chem. Soc. Commun. 1761-1762.
Sasson et al. (2003) "Novel Method for Incorporating the CHF2 Group into Organic Molecules Using BrF3" Organic Letters 5(5):769-771.
Scheeren et al. (1973) "A General Procedure for the Conversion of a Carbonyl Group into a Thione Group with Tetraphosphorus Decasulfide" Communications 149-151.
Seergeva and Dolbier (2004) "A New Synthesis of Pentafluorosulfanylbenzene" Organic Letters 6(14):2417-2419.
Sharts and Sheppard (1974) "Modern Methods to Prepare Monofluoroaliphatic Compounds" Organic Chemistry 21:158-173.
Sheppard (1962) "Arylsulfur Pentafluorides" J. Am. Chem. Soc. 84:3064-3072.
Sheppard (1962) "Alkyl- and Arylsulfur Trifluorides" J. Chem. Soc. 84:3058-3063.
Sheppard (1973) "Phenylsulfur Tri Fluoride" Organic Syntheses, Coll. 5:959; (1964) 44:82.
Sheppard and Foster (1972) "Pentafluorophenylsulfur(IV) Derivatives" Journal of Fluorine Chemistry 2:53-61.
Sheppard and Taft (1972) "The Electronic Properties of Di-, Tri-, Tetra-, and Hexacoordinate Sulfur Substituents" Journal Am. Chem. Soc. 94(6)1919-1923.
Shimizu et al. (1995) "Gem-Difluorination of 1,3-Dithiolanes with the Hexafluoropropene-Diethylamine reagent and N-Iodosuccinimide or 1,3-Dibromo-5,5-Dimethylhydantoin" Journal of Fluorine Chemistry 71:9-12.
Simons and Lewis (1938) "The Preparation of Benzotrifluoride" J. Am. Chem. Soc. 60(2):492.
Sipyagin et al. (2001) "Preparation of the First Ortho-Substituted Pentafluorosulfanylbenzenes" Journal of Fluorine Chemistry 112:287-295.
Smith et al. (1960) "Chemistry of Sulfur Tetrafluoride. III. Organoiminosulfur Difluorides" Journal of American Chem. Soc. 82(3):551-555.
Sondej and Katzenellenbogen (1986) "Gem-Difluoro Compounds: A Convenient Preparation from Ketones and Aldehydes by Halogen Fluoride Treatment of 1,3-Dithiolanes" J. Org. Chem. 51:3508-3513.
Tarrant et al. (1954) "Fluoroölefins. V. The Synthesis of 1,1-Difluoro-3-Methylbutadiene" J. Am. Chem. Soc. 76(9): 2343-2345.
Thayer (2006) "Fabulous Fluorine" Chemical & Engineering News 84(23):15-24.
Thayer (2006) "Constructing Life Sciences Compounds" Chemical & Engineering News 84(23):27-32.
Tordeux et al. (1990) "Reactions of trifluoromethyl bromide and related halides: part 9. Comparison between additions to carbonyl compounds, enamines, and sulphur dioxide in the presence of zinc" J. Chem. Soc., Perkin Trans. 1 1951-1957.
Tozer and Herpin (1996) "Methods for the Synthesis of gem-Difluoromethylene Compounds" Tetrahedron 52(26): 8619-8683.
Tullock (1960) "The Chemistry of Sulfur Tetrafluoride. I. The Synthesis of Sulfur Tetrafluoride" Journal of American Chem. Soc. 82(3):539-542.
Uneyama (2006) "Nucleophilic Substitution on Fluoroaromatic Rings" Organofluorine Chemistry, Blackwell Publishing Ltd., Oxford, UK (ISBN-13: 978-14051-2561-1) pp. 101-107.
Whitham, Gordon H. (1995) "Organosulfur Chemistry" Oxford Chemistry Primers, 33, Oxford Science Publications, Chapter 3, pp. 34-63 (ISBN-13: 9780198558996).
Winter and Gard (2004) "Synthesis of SF5-benzene (SF5C6H5) by the SF5-halide Method" Journal of Fluorine Chem. 125:549-552.
Yoshiyama and Fuchigami (1992) "Anodic gem-Difluorination of Dithioacetals" Chemistry Letters 1995-1998.
Xiaobo et al. (1997) "Oxidative Addition and Isomerization Reactions—The Synthesis of cis-ArSF4Cl and trans-ArSF4Cl and cis-PhTeF4Cl and trans-PhTeF4Cl" Canadian Journal of Chemistry, 75(12):1878-1884.
Umemoto et al (2010) "Discovery of 4-tert-Butyl-2,6-dimethylphenylsulfur Trifluoride as a Deoxofluorinating Agent with High Thermal Stability as Well as Unusual Resistance to Aqueous Hydrolysis, and Its Diverse Fluorination Capabilities Including Deoxofluoro-Arylsulfinylation with High Stereoselectivity" JACS 132:18199-18205.
Ariyan and Wiles (1961) Journal of Chemical Society 888:4510-4514 "The Action of Sulphur Monochloride on Aromatic Hydrocarbons".
European Search Report from EP 12153153, dated May 25, 2012, 7 pages.
European Search Report from EP 12153156, dated May 25, 2012, 7 pages.
European Search Report from EP 12153157, dated May 25, 2012, 7 pages.
European Search Report from EP 12153158, dated May 25, 2012, 8 pages.
Tsuchida et al. (1993) Macromolecules 26:4113-4117 "Thermal Polymerization of Diaryl Disulfides to Yield Poly(arylene sulfide)s".
Yamamoto et al. (1991) J. Chem. Soc., Chem. Commun. 8:596-597 "One-pot Synthesis of Poly(thioarylene)s: Predominant Sulphide Bond Formation through Oxidative and Electrophilic Reaction".

\* cited by examiner

PROCESSES FOR PREPARING POLY(PENTAFLUOROSULFANYL)AROMATIC COMPOUNDS

RELATED APPLICATIONS

This application is a 35 U.S.C. §371 national phase application of PCT/US2009/057714 (WO 2010/033930), filed on Sep. 21, 2011, entitled "Processes for Preparing Poly(Pentafluorosulfanyl)Aromatic Compounds", which application claims the benefit of U.S. Provisional Application Ser. No. 61/098,975, filed Sep. 22, 2008, entitled "Processes For Preparing Poly(Pentafluorosulfanyl) Aromatic Compounds" and U.S. Provisional Application Ser. No. 61/143,564, filed Jan. 9, 2009, entitled "Processes For Preparing Poly(Pentafluorosulfanyl)Aromatic Compounds", each of which is incorporated herein by reference in its entirety.

TECHNICAL FIELD

The invention relates to methods for preparing an aromatic compound substituted with two or three pentafluorosulfanyl groups.

BACKGROUND OF THE INVENTION

Arylsulfur pentafluorides compounds are used to introduce one or more sulfur pentafluoride groups into various organic molecules in the development of medicines, agrochemicals, and new materials. In particular, arylsulfur pentafluorides have been shown as useful compounds (as product or intermediate) in the development of liquid crystals, in bioactive chemicals such as fungicides, herbicides, and insecticides, and in other like materials [see Fluorine-containing Synthons (ACS Symposium Series 911), ed by V. A. Soloshonok, American Chemical Society (2005), pp. 108-113]. In particular, aromatic compounds having two or more pentafluorosulfanyl groups ($SF_5$) are of increased interest because they are more useful in these applications as compared to aromatic compounds having one pentafluorosulfanyl group. Presently, few such compounds have been successfully synthesized, for example 3,5-bis(pentafluorosulfanyl)nitrobenzene, 3,5-bis(pentafluorosulfanyl)aniline, 1,3,5-tris(pentafluorosulfanyl)benzene, and 1,2,4-tris(pentafluorosulfanyl)benzene have been synthesized to date, illustrating the difficulty of their production. As such, and as discussed further herein, conventional synthetic methodologies to prepare aromatic compounds having two or three pentafluorosulfanyl groups have proven difficult to prepare and are a concern within the art.

Conventionally, aromatic compounds having two or three pentafluorosulfanyl groups are synthesized by one of the following methods: (1) fluorination of a poly(nitrobenzenedisulfide) with $AgF_2$ [see J. Am. Chem. Soc., Vol. 82 (1962), pp. 3064-3072]; or (2) reaction of $SF_5Cl$ with acetylene, followed by bromination with $Br_2$ under hv irradiation, dehydrobromination, and reduction with zinc, giving pentafluorosulfanylacetylene ($HC\equiv CSF_5$). The pentafluorosulfanylacetylene is then reacted with $Co_2(CO)_8$, giving a complex, $Co(CO)_4(HC\equiv CSF_5)_3$, and the complex decomposing in the presence of $Br_2$ to give 1,2,4-tris(pentafluorosulfanyl)benzene [see Chem. Ber., Vol. 119, pp. 453-463 (1986)]. Photoreaction of pentafluorosulfanylacetylene in the presence of $SF_5Cl$ gives 1,3,5-tris(pentafluorosulfanyl)benzene [see Chem. Ber., Vol. 119, pp. 453-463 (1986)].

Each of the above synthetic methods has one or more drawbacks making them industrially impractical. For example, the former method provides a very low yield and requires an expensive reaction agent, $AgF_2$. The latter method requires an expensive and toxic gas, $SF_5Cl$, and many reaction steps to reach a final product at low yield.

In addition, it has been reported that related compounds, p- and m-(pentafluorosulfanyl)nitrobenzene, were prepared by reacting a bis(nitrophenyl) disulfide with molecular fluorine ($F_2$), $CF_3OF$, or $CF_2(OF)_2$ [Tetrahedron, Vol. 56, 3399-3408 (2000); USP 2004/0249209 A1]. However, $F_2$, $CF_3OF$, and/or $CF_2(OF)_2$ are extremely toxic, corrosive, and dangerous gasses and their handling is expensive from the standpoint of gas production, storage and use. In addition, synthesis methods that require the use of $F_2$, $CF_3OF$, and/or $CF_2(OF)_2$ are limited to the production of deactivated (pentafluorosulfanyl)aromatic compounds, such as nitro-substituted (pentafluorosulfanyl)aromatic compounds, due to their extreme reactivity, which leads to side-reactions such as fluorination of the aromatic rings when not deactivated. It has also been reported that (pentafluorosulfanyl)benzene and p-(pentafluorosulfanyl)toluene were prepared by reacting diphenyl disulfide and di(p-tolyl) disulfide with $XeF_2$, respectively [J. Fluorine Chem., Vol. 125 (2004), pp. 549-552]. However, this method requires an expensive reagent, $XeF_2$. Therefore, problems with the production methods known for the pentafluorosulfanylaromatic compounds have made it difficult to prepare the material in an industrially safe, cost effective and timely fashion.

The present invention is directed toward overcoming one or more of the problems discussed above.

SUMMARY OF THE INVENTION

The present invention provides novel processes for the production of poly(pentafluorosulfanyl)aromatic compounds, as represented by formula (I):

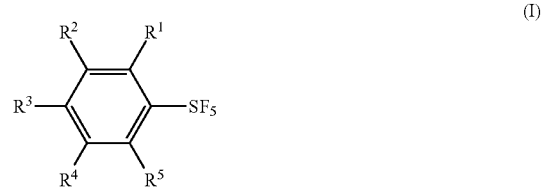

in which one or two of $R^1$, $R^2$, $R^3$, $R^4$, and $R^5$ are a pentafluorosulfanyl ($SF_5$) group and each of the remainders is selected from a group consisting of a hydrogen atom, a halogen atom, a substituted or unsubstituted alkyl group having 1 to 18 carbon atoms, a nitro group, and a cyano group.

Embodiments of the invention include reacting an aryl sulfur compound, having a formula (II):

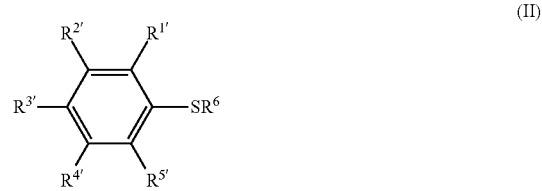

in which one or two of $R^{1'}$, $R^{2'}$, $R^{3'}$, $R^{4'}$, and $R^{5'}$ are a $SR^6$ group and each of the remainders is selected from a group consisting of a hydrogen atom, a halogen atom, a substituted or unsubstituted alkyl group having 1 to 18 carbon atoms, a nitro group, and a cyano group, and $R^6$ is a hydrogen atom, a silyl group, a metal atom, an ammonium moiety, a phosphonium moiety, or a halogen atom, or $R^6$ combines with another $R^6$ of its own molecule or another molecule to form a single bond;

with a halogen selected from the group of chlorine, bromine, iodine and interhalogens, and a fluoro salt ($M^+F^-$, formula III) to form a poly(halotetrafluorosulfanyl)aromatic compound. The poly(halotetrafluorosulfanyl)aromatic compound has a formula (IV):

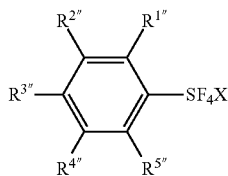

(IV)

in which one or two of $R^{1''}$, $R^{2''}$, $R^{3''}$, $R^{4''}$, and $R^{5''}$ are a $SF_4X$ group and each of the remainders is selected from a group consisting of a hydrogen atom, a halogen atom, a substituted or unsubstituted alkyl group having 1 to 18 carbon atoms, a nitro group, and a cyano group, and X is a chlorine atom, a bromine atom, or an iodine atom.

Poly(halotetrafluorosulfanyl)aromatic compounds (formula IV) are reacted with a fluoride source to form poly(pentafluorosulfanyl)aromatic compounds (formula I).

Embodiments of the present invention also provide processes for producing a poly(pentafluorosulfanyl)aromatic compound (formula I) by reacting an aryl sulfur compound, having a formula (II), with a halogen selected from the group of chlorine, bromine, iodine, and interhalogens, and a fluoro salt ($M^+F^-$, formula III) to form a poly(halotetrafluorosulfanyl)aromatic compound having a formula (IV). The poly(halotetrafluorosulfanyl)aromatic compound (formula IV) is reacted with a fluoride source in the presence of a halogen selected from the group of chlorine, bromine, iodine, and interhalogens to form a poly(pentafluorosulfanyl)aromatic compound (formula I).

Embodiments of the present invention also provide processes for producing poly(pentafluorosulfanyl)aromatic compounds (formula I) by reacting an arylsulfur trifluoride having a formula (V):

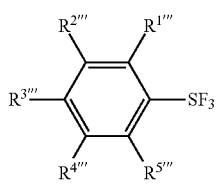

(V)

in which one or two of $R^{1'''}$, $R^{2'''}$, $R^{3'''}$, $R^{4'''}$, and $R^{5'''}$ are a $SF_3$ group and each of the remainders is selected from a group consisting of a hydrogen atom, a halogen atom, a substituted or unsubstituted alkyl group having 1 to 18 carbon atoms, a nitro group, and a cyano group;

with a halogen selected from the group of chlorine, bromine, iodine and interhalogens, and a fluoro salt (formula III) to form a poly(halotetrafluorosulfanyl)aromatic compound having a formula (IV). The poly(halotetrafluorosulfanyl)aromatic compound (formula IV) is reacted with a fluoride source to form a poly(pentafluorosulfanyl)aromatic compound (formula I).

Embodiments of the present invention also provide processes for producing poly(pentafluorosulfanyl)aromatic compounds (formula I) by reacting an arylsulfur trifluoride having a formula (V) with a halogen selected from the group of chlorine, bromine, iodine and interhalogens, and a fluoro salt (formula III) to form a poly(halotetrafluorosulfanyl)aromatic compound having a formula (IV). The poly(halotetrafluorosulfanyl)aromatic compound (formula IV) is reacted with a fluoride source in the presence of a halogen selected from the group of chlorine, bromine, iodine, and interhalogens to form a poly(pentafluorosulfanyl)aromatic compound (formula I).

Embodiments of the present invention further provide processes for producing a poly(halotetrafluorosulfanyl)aromatic compound (formula IV) by reacting an aryl sulfur compound having a formula (II) with a halogen selected from a group of chlorine, bromine, iodine and interhalogens, and a fluoro salt having a formula (III) to form an poly(halotetrafluorosulfanyl)aromatic compound having a formula (IV).

Embodiments of the present invention provide processes for producing a poly(halotetrafluorosulfanyl)aromatic compound (formula IV) by reacting an arylsulfur trifluoride having a formula (V) with a halogen selected from a group of chlorine, bromine, iodine and interhalogens, and a fluoro salt having a formula (III) to form an poly(halotetrafluorosulfanyl)aromatic compound having a formula (IV).

Embodiments of the present invention provide processes for producing a poly(pentafluorosulfanyl)aromatic compound (formula I) by reacting a poly(halotetrafluorosulfanyl) aromatic compound having a formula (IV) with a fluoride source to form a poly(pentafluorosulfanyl)aromatic compound.

In addition, embodiments of the present invention provide processes for producing a poly(pentafluorosulfanyl)aromatic compound (formula I) by reacting a poly(halotetrafluorosulfanyl)aromatic compound having a formula (IV) with a fluoride source in the presence of a halogen selected from the group of chlorine, bromine, iodine, and interhalogens to form a poly(pentafluorosulfanyl)aromatic compound.

Embodiments of the present invention also provide processes for producing a halogenated poly(pentafluorosulfanyl) aromatic compound as represented by formula (I)($R^2$=Y) by reacting a poly(pentafluorosulfanyl)aromatic compound having a formula (I)($R^2$=H) with a halogenating agent and an acid to form the poly(pentafluorosulfanyl)aromatic compound of formula (I)($R^2$=Y).

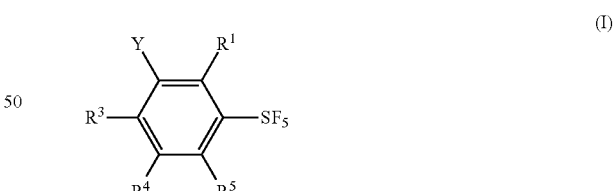

($R^2$ = Y)

(I)

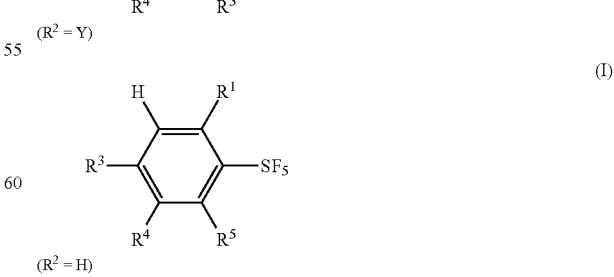

($R^2$ = H)

(I)

in which Y is a halogen atom which is a fluorine atom, chlorine atom, bromine atom, or iodine atom; and one or two of $R^1$, $R^3$, $R^4$, and $R^5$ are a pentafluorosulfanyl ($SF_5$) group and each of the remainders is selected from a group consisting of a hydrogen atom, a halogen atom, a substituted or unsubstituted alkyl group having 1 to 18 carbon atoms, a nitro group, and a cyano group.

In addition, the present invention provides novel poly (chlorotetrafluorosulfanyl)aromatic compounds represented by formula (IV'):

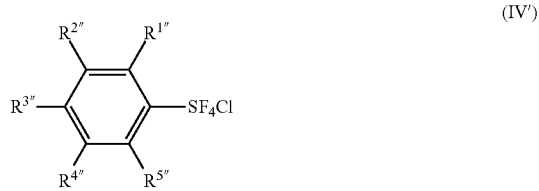

wherein one or two of $R^{1''}$, $R^{2''}$, $R^{3''}$, $R^{4''}$, and $R^{5''}$ are $SF_4Cl$ and each of the remainders is a hydrogen atom, a halogen atom, a substituted or unsubstituted alkyl group having 1 to 18 carbon atoms, preferably 1 to 10 carbon atoms, more preferably 1 to 4 arbon atoms, a nitro group, or a cyano group.

Finally, the present invention provides novel bis(pentafluorosulfanyl)benzene compounds represented by formula (I''):

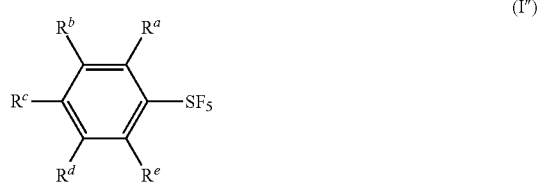

wherein one of $R^a$, $R^b$, $R^c$, $R^d$, and $R^e$ is a $SF_5$ group and each of the remainders is selected from a group consisting of a hydrogen atom and a halogen atom.

These and various other features as well as advantages which characterize embodiments of the invention will be apparent from a reading of the following detailed description and a review of the appended claims.

DETAILED DESCRIPTION OF THE INVENTION

Embodiments of the present invention provide industrially useful processes for producing poly(pentafluorosulfanyl)aromatic compounds, as represented by formula (I). Poly(pentafluorosulfanyl)aromatic compounds can be used as products or intermediates in the development of bioactive chemicals, in the materials science, and in other like applications. Unlike previous methods in the art, the processes of the invention utilize short processes, i.e., limited number of steps, and low cost reagents to prepare better yields of poly(pentafluorosulfanyl)aromatic compounds. Further, methods of the invention provide a greater degree of overall safety in comparison to most prior art methodologies (for example methodologies that require the use of $F_2$ gas).

A distinction of the present invention is that the processes herein are accomplished at a low cost as compared to other conventional methods. For example, the reagents to perform silver or xenon based reactions are cost prohibitive, whereas the present invention utilizes relatively cheap materials: for example, a halogen such as chlorine ($Cl_2$) and a fluoro salt such as potassium fluoride (KF).

Embodiments of the invention include processes which comprise (see for example Scheme 1, Processes I and II) reacting an aryl sulfur compound having a formula (II) with a halogen selected from the group of chlorine, bromine, iodine, and interhalogens, and a fluoro salt having a formula (III), to form a poly(halotetrafluorosulfanyl)aromatic compound, represented by formula (IV). The poly(halotetrafluorosulfanyl)aromatic compound is then reacted with a fluoride source to form poly(pentafluorosulfanyl)aromatic compounds having a formula (I).

Scheme 1: (Processes I and II)

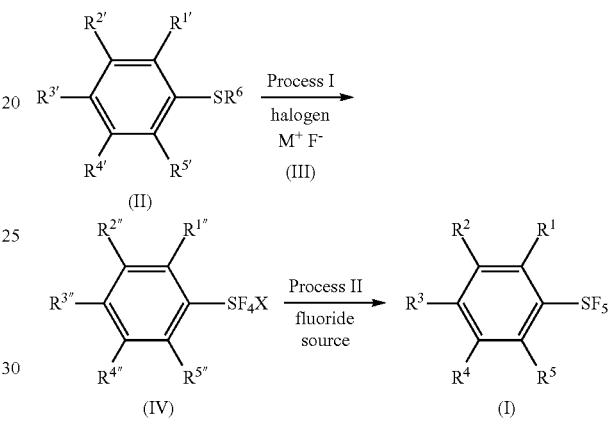

With regard to formulas (I), (II), (III), and (IV): one or two of $R^1$, $R^2$, $R^3$, $R^4$, and $R^5$ are a $SF_5$ group and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group; one or two of $R^{1'}$, $R^{2'}$, $R^{3'}$, $R^{4'}$, and $R^{5'}$ are a $SR^6$ group and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group; one or two of $R^{1''}$, $R^{2''}$, $R^{3''}$, $R^{4''}$, and $R^{5''}$ are a $SF_4X$ group and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group; and $R^6$ is a hydrogen atom, a silyl group, a metal atom, an ammonium moiety, a phosphonium moiety, or a halogen atom or $R^6$ combines with another $R^6$ of its own molecule or another molecule to form a single bond. The halogen atom herein is a fluorine atom, a chlorine atom, a bromine atom, or an iodine atom.

With regard to M, M is a metal atom, an ammonium moiety, or a phosphonium moiety; with regard to X, X is a chlorine atom, a bromine atom, or an iodine atom.

The term "alkyl" as used herein is a linear, branched, or cyclic alkyl. The term "substituted alkyl" as used herein means an alkyl moiety having one or more substituents such as a halogen atom, a substituted or unsubstituted aryl group, and/or any other group with or without a heteroatom(s) such as an oxygen atom(s), a nitrogen atom(s), and/or a sulfur atom(s), which does not limit reactions of this invention.

Poly(halotetrafluorosulfanyl)aromatic compounds of formula (IV) include stereoisomers composed of trans-conformation and cis-conformation based on a SF₄X substituent as shown below; an aromatic compound having a SF₄X group is represented by ArSF₄X:

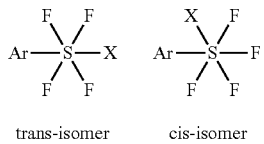

trans-isomer    cis-isomer

Aromatic compounds having two SF₄X substituents of this invention, as represented by XF₄S-Arylene-SF₄X, are shown as follows;

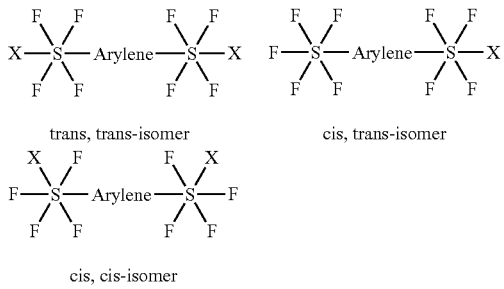

Similarly, aromatic compounds having three SF₄X groups of this invention include stereoisomers such as trans,trans,trans-isomers, trans,trans,cis-isomers, trans,cis,cis-isomers, and cis,cis,cis-isomers.

Table 1 provides structure names and formulas for reference when reviewing Schemes 1, 3~10:

TABLE 1

Formulas (I), (II), (III), (IV), (V), (I)(R² = Y), and (I)(R² = H)

| Name | Structure/Formula Number |
|---|---|
| Poly(pentafluorosulfanyl)-aromatic compound | (I) |
| Aryl sulfur compound | (II) |
| Fluoro salt | M⁺F⁻ (III) |
| Poly(halotetrafluoro-sulfanyl)aromatic compound | (IV) |
| Arylsulfur trifluoride | (V) |
| Halogenated poly(pentafluorosulfanyl)-aromatic compound | (I)(R² = Y) |
| Hydro poly(pentafluorosulfanyl)-aromatic compound | (I)(R² = H) |

Process I (Scheme 1)

Process I includes reacting an aryl sulfur compound, having a formula (II), with a halogen selected from the group of chlorine, bromine, iodine and interhalogens, and a fluoro salt (M⁺F⁻, formula III) to form a poly(halotetrafluorosulfanyl) aromatic compound having a formula (IV).

When one or two of $R^{1'}$, $R^{2'}$, $R^{3'}$, $R^{4'}$, and $R^{5'}$ are a $SR^6$ group, $R^6$ is a hydrogen atom, a silyl group, a metal atom, an ammonium moiety, or a phosphonium moiety, and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group; illustrative aryl sulfur compounds, as represented by formula (II), of the invention include, but are not limited to: each isomer of benzenedithiol, each isomer of methylbenzenedithiol, each isomer of ethylbenzenedithiol, each isomer of n-propylbenzenedithiol, each isomer of isopropylbenzenedithiol, each isomer of n-butylbenzenedithiol, each isomer of sec-butylbenzenedithiol, each isomer of isobutylbenzenedithiol, each isomer of tert-butylbenzenedithiol, each isomer of pentylbenzenedithiol, each isomer of hexylbenzenedithiol, each isomer of heptylbenzenedithiol, each isomer of octylbenzenedithiol, each isomer of nonylbenzenedithiol, each isomer of decylbenzenedithiol, each isomer of fluorobenzenedithiol, each isomer of difluorobenzenedithiol, each isomer of trifluorobenzenedithiol, each isomer of tetrafluorobenzenedithiol, each isomer of chlorobenzenedithiol, each isomer of bromobenzenedithiol, each isomer of iodobenzenedithiol, each isomer of nitrobenzenedithiol, each isomer of cyanobenzenedithiol, each isomer of benzenetrithiol, each isomer of fluorobenzenetrithiol, each isomer of difluorobenzenetrithiol, each isomer of trifluorobenzenetrithiol, and other like compounds; S-trimethylsilyl, S-triethylsilyl, S-tripropylsilyl, S-dimethyl-tert-butylsilyl, and S-dimethylphenylsilyl derivatives of the benzenedithiol or benzenetrithiol compounds exemplified here; lithium, sodium, and potassium salts of the benzendithiol or benzenetrithiol compounds exemplified here; ammonium, diethylammonium, triethylammonium, trimethylammonium, tetramethylammonium, tetraethylammonium, tetrapropylammonium, and tetrabutylammonium salts of the benzenedithiol or benzenetrithiol compounds exemplified here; tetramethylphosphonium, tetraethylphosphonium, tetrapropylphosphonium, tetrabutylphosphonium, and tetraphenylphosphonium salts of the benzenedithiol or benzenetrithiol compounds exemplified here. Examples of aryl sulfur compounds of formula (II), where $R^6$ is a halogen atom, are each isomer of benzenedi(sulfenyl chloride), each isomer of nitrobenzenedi(sulfenyl chloride), and other like compounds. Each of the above formula (II) compounds can be prepared in accordance with understood principles of synthetic chemistry or according to the literature [see for example J. Org. Chem., Vol. 46, pp. 3070-3073 (1981); Chem. Ber. Vol. 106, pp. 719-720 (1973); Chem. Ber., Vol. 106, pp. 2419-2426 (1973); J. Org. Chem., Vol. 45, pp. 4376-4380 (1980), each of which is incorporated herein by reference for all purposes] or may be available from appropriate vendors (see for example Sigma-Aldrich, Acros, TCI, Lancaster, Alfa Aesar, etc.).

When one or two of $R^{1'}$, $R^{2'}$, $R^{3'}$, $R^{4'}$, and $R^{5'}$ are $SR^6$, $R^6$ can combine with another $R^6$ of its own molecule or another molecule to form a single bond, and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group; illustrative aryl sulfur compounds, as represented by formula (II), include, but are not limited to: polymeric or dimeric compounds of units exemplified by the following formulas:

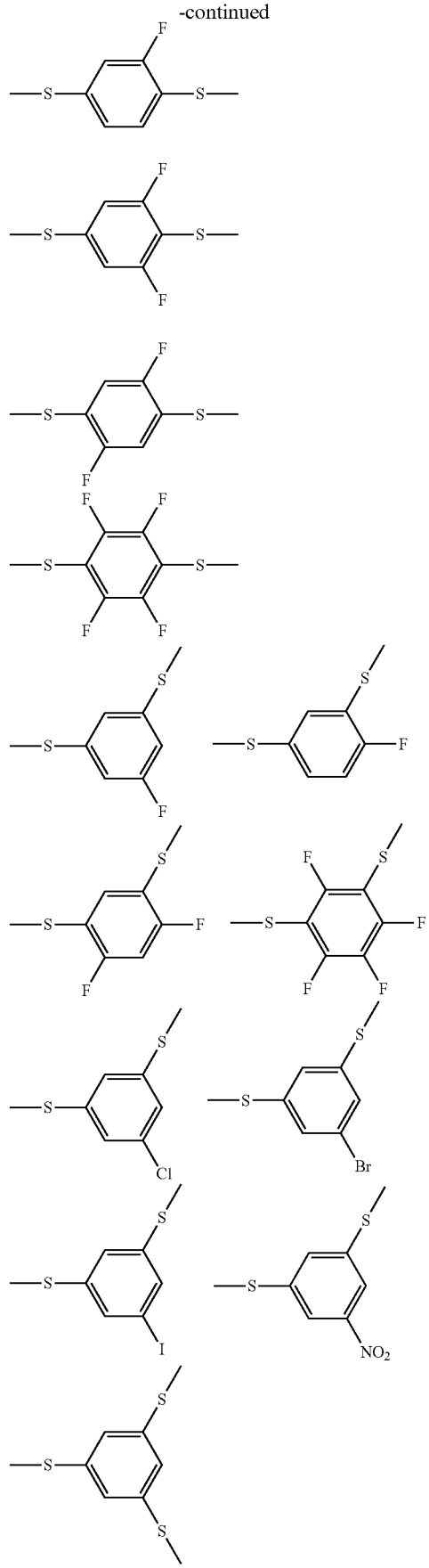

Each of the above formula (II) compounds of the polymeric or dimeric compounds can be prepared in accordance with understood principles of synthetic chemistry or according to the literatures [see for example J. Am. Chem. Soc., Vol. 82, pp. 3064-3072 (1962), incorporated herein by reference for all purposes].

Typical halogens employed in the present invention include: chlorine ($Cl_2$), bromine ($Br_2$), iodine ($I_2$), and interhalogens such as ClF, BrF, ClBr, ClI, $Cl_3I$, and BrI. Among these, chlorine ($Cl_2$) is preferable due to its relative low cost.

Fluoro salts, having a formula (III), are those which are easily available and are exemplified by metal fluorides, ammonium fluorides, and phosphonium fluorides. Process I can be carried out using one or more fluoro salts. Examples of suitable metal fluorides are alkali metal fluorides such as lithium fluoride, sodium fluoride, potassium fluoride (including spray-dried potassium fluoride), rubidium fluoride, and cesium fluoride. Examples of suitable ammonium fluorides are tetramethylammonium fluoride, tetraethylammonium fluoride, tetrapropylammonium fluoride, tetrabutylammonium fluoride, benzyltrimethylammonium fluoride, benzyltriethylammonium fluoride, and so on. Examples of suitable phosphonium fluorides are tetramethylphosphonium fluoride, tetraethylphosphonium fluoride, tetrapropylphosphonium fluoride, tetrabutylphosphonium fluoride, tetraphenylphosphonium fluoride, tetratolylphosphonium fluoride, and so on. The alkali metal fluorides, such as potassium fluoride and cesium fluoride, and ammonium fluorides, such as tetramethylammonium fluoride and tetrabutylammonium fluoride, are preferable from the viewpoint of availability and capacity to result in high yield, and potassium fluoride is most preferable from the viewpoint of cost.

Fluoro salts (formula III) can be used as a mixture of a metal fluoride and an ammonium fluoride or a phosphonium fluoride, a mixture of an ammonium fluoride and a phosphonium fluoride, or a mixture of a metal fluoride, an ammonium fluoride, and a phosphonium fluoride.

As a fluoro salt (formula III), there can also be used a mixture of a metal fluoride and an ammonium salt having an anion part other than $F^-$; a mixture of a metal salt having an anion part other than $F^-$ and an ammonium fluoride; a mixture of a metal fluoride and a phosphonium salt having an anion part other than $F^-$; a mixture of a metal salt having an anion part other than $F^-$ and a phosphonium fluoride; a mixture of an ammonium fluoride and a phosphonium salt having an anion part other than $F^-$; or a mixture of an ammonium salt having an anion part other than $F^-$ and a phosphonium fluoride. Furthermore, there can be a mixture of a metal fluoride, an ammonium fluoride, and a phosphonium salt having an anion part other than $F^-$; a mixture of a metal fluoride, an ammonium salt having an anion part other than $F^-$, and a phosphonium fluoride; a mixture of a metal salt having an anion part other than $F^-$, an ammonium fluoride, and a phosphonium fluoride; a mixture of a metal fluoride, an ammonium salt having an anion part other than $F^-$, and a phosphonium salt having an anion part other than $F^-$, and so on. These salts can undertake a mutual exchange reaction of the anion parts between and among themselves (for example, see Scheme 2).

Scheme 2: Mutual anion exchange reaction between salts

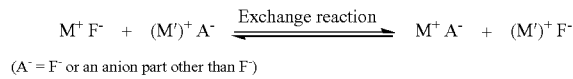

($A^-$ = $F^-$ or an anion part other than $F^-$)

The combination of these salts may accelerate the reactions in Process I, because the reaction may depend on the solubility of the fluoro salts to the solvent used. As such, a high concentration of fluoride anions ($F^-$) will increase the available fluoride anion during the reaction. Therefore, one may choose a suitable combination of these salts in order to increase the effective concentration of $F^-$. The amount (used against the amount of the metal fluoride, ammonium fluorides, and/or phosphonium fluorides) of the metal, ammonium, and phosphonium salts having anion parts other than $F^-$, can be chosen from a catalytic amount to any amount that does not interfere with the reactions or does not dramatically decrease the yield of the products. The anion parts other than $F^-$ can be chosen from any anions which do not limit the reactions or do not so decrease the yields of the products. Examples of the anion parts other than $F^-$ include, but are not limited to: $Cl^-$, $Br^-$, $I^-$, $BF_4^-$, $PF_6^-$, $SO_4^-$, $OCOCH_3^-$, $OCOCF_3^-$, $^-OSO_2CH_3$, $^-OSO_2CF_3$, $^-OSO_2C_4F_9$, $^-OSO_2C_6H_5$, $^-OSO_2C_6H_4CH_3$, $^-OSO_2C_6H_4Br$, and so on. Among them, the anion parts (other than F) which do not have an oxygen anion(s) are preferable, and $Cl^-$, $BF_4^-$ and $PF_6^-$ are more preferable because of relatively high yield reactions. In addition, $Cl^-$ is most preferable because of its cost.

From the viewpoint of efficiency and yields of the reactions, Process I is preferably carried out in the presence of one or more solvents. The solvent is preferably an inert, polar, aprotic solvent. A preferable solvent will not substantially react with the starting materials and reagents, the intermediates, and/or the final products. Suitable solvents include, but are not limited to, nitriles, ethers, nitro compounds, and so on, and mixtures thereof. Illustrative nitriles are acetonitrile, propionitrile, benzonitrile, and so on. Illustrative ethers are tetrahydrofuran, diethyl ether, dipropyl ether, dibutyl ether, t-butyl methyl ether, dioxane, glyme, diglyme, triglyme, and so on. Illustrative nitro compounds are nitromethane, nitroethane, nitropropane, nitrobenzene, and so on. Acetonitrile is a preferred solvent for use in Process I from a viewpoint of providing relatively higher yields of the products, as compared to other suitable solvents.

In order to obtain good yields of product in Process I, the reaction temperature can be selected in the range of about $-60°$ C.$\sim+70°$ C. More preferably, the reaction temperature can be selected in the range of about $-40°$ C.$\sim+50°$ C. Furthermore preferably, the reaction temperature can be selected in the range of about $-20°$ C.$\sim+40°$ C.

Reaction conditions of Process I are optimized to obtain economically good yields of product. When one of $R^{1'}$, $R^{2'}$, $R^{3'}$, $R^{4'}$, and $R^{5'}$ is $SR^6$ ($R^6$=a hydrogen atom, a silyl group, a metal atom, an ammonium moiety, or a phosphonium moiety), about 6 mol to about 30 mol of halogen are combined with about 1 mol of aryl sulfur compound (formula II) to obtain a good yield of a poly(halotetrafluorosulfanyl)aromatic compound (formula IV). When two of $R^{1'}$, $R^{2'}$, $R^{3'}$, $R^{4'}$, and $R^{5'}$ are $SR^6$ ($R^6$=a hydrogen atom, a silyl group, a metal atom, an ammonium moiety, or a phosphonium moiety), about 9 mol to about 45 mol of halogen are combined with about 1 mol of aryl sulfur compound (formula II) to obtain a good yield of a poly(halotetrafluorosulfanyl)aromatic compound (formula IV).

When one of $R^{1'}$, $R^{2'}$, $R^{3'}$, $R^{4'}$, and $R^{5'}$ is $SR^6$ ($R^6$=a halogen atom), about 4 mol to about 20 mol of halogen are combined with about 1 mol of aryl sulfur compound (formula II) to obtain a good yield of a poly(halotetrafluorosulfanyl)aromatic compound (formula IV). When two of $R^{1'}$, $R^{2'}$, $R^{3'}$, $R^{4'}$, and $R^{5'}$ is $SR^6$ ($R^6$=a halogen atom), about 6 mol to about 30 mol of halogen are combined with about 1 mol of aryl sulfur compound (formula II) to obtain a good yield of a poly(halotetrafluorosulfanyl)aromatic compound (formula IV).

When one of $R^{1'}$, $R^{2'}$, $R^{3'}$, $R^{4'}$, and $R^{5'}$ are $SR^6$ in which $R^6$ forms a single bond with another $R^6$, about 5 mol to about 25 mol of halogen are combined with about 1 mol of one unit of aryl sulfur compound (formula II) to obtain a good yield of a poly(halotetrafluorosulfanyl)aromatic compound (formula IV). When two of $R^{1'}$, $R^{2'}$, $R^{3'}$, $R^{4'}$, and $R^{5'}$ are $SR^6$ in which $R^6$ forms a single bond with another $R^6$, about 7.5 mol to about 37.5 mol of halogen are combined with about 1 mol of one unit of aryl sulfur compound (formula II) to obtain a good yield of a poly(halotetrafluorosulfanyl)aromatic compound (formula IV).

When one of $R^{1'}$, $R^{2'}$, $R^{3'}$, $R^{4'}$, and $R^{5'}$ is $SR^6$, the amount of a fluoro salt (formula III) used in embodiments of Process I can be in the range of from about 8 to about 40 mol against 1 mol of aryl sulfur compound or 1 mol of a unit of aryl sulfur compound of formula (II) to obtain economically good yields of product. When two of $R^{1'}$, $R^{2'}$, $R^{3'}$, $R^{4'}$, and $R^{5'}$ are $SR^6$, the amount of a fluoro salt (formula III) used in embodiments of Process I can be in the range of from about 12 to about 60 mol against 1 mol of aryl sulfur compound or 1 mol of a unit of aryl sulfur compound of formula (II) to obtain economically good yields of product.

Note that the reaction time of Process I varies dependent upon reaction temperature, and the types and amounts of substrates, reagents, and solvents. As such, reaction time is generally determined as the amount of time required to complete a particular reaction, but can be from about 0.5 hour (h) to several days, preferably, within a few days.

Process II (Scheme 1)

Embodiments of the invention include Process II, a reaction of a poly(halotetrafluorosulfanyl)aromatic compound, obtained in Process I, with a fluoride source, as shown in Scheme 1.

Fluoride sources employable in Process II are compounds that display fluoride activity to the poly(halotetrafluorosulfanyl)aromatic compounds (formula IV). Anhydrous fluoride sources are used preferably because byproducts, arylsulfonyl fluorides [aromatic compounds with a $SO_2F$ substituent(s)], are not formed or their formation is suppressed. The $SO_2F$ substituent may be derived from a $SF_4X$ substituent when water molecules ($H_2O$) are present.

Process II can be carried out using one or more fluoride sources. The fluoride sources can be selected from fluorides of typical elements in the Periodic Table, fluorides of transition elements in the Periodic Table, and mixture or compounds between or among these fluorides of typical elements and/or transition elements.

The fluoride sources include mixtures or compounds of fluoride sources with fluoride source-activating compounds. The combination of a fluoride source and a fluoride source-activating compound is beneficial to cost performance, because a relatively cheap fluoride source-activating compound can activate a relatively cheap fluoride source, which will not work satisfactorily by itself, as a fluoride source for the poly(halotetrafluorosulfanyl)aromatic compound (formula IV) (owing to its low reactivity).

In addition, the fluoride source may be a mixture, salt, or complex with an organic molecule(s) that does(do) not limit the reactions of this invention.

Suitable examples of fluorides of the typical elements include fluorides of Element 1 in the Periodic Table such as hydrogen fluoride (HF) and alkali metal fluorides, LiF, NaF, KF, RbF, and CsF; fluorides of Element 2 (alkali earth metal fluorides) such as $BeF_2$, $MgF_2$, $MgFCl$, $CaF_2$, $SrF_2$, $BaF_2$ and so on; fluorides of Element 13 such as $BF_3$, $BF_2Cl$, $BFCl_2$, $AlF_3$, $AlF_2Cl$, $AlFCl_2$, $GaF_3$, $InF_3$, and so on; fluorides of Element 14 such as $SiF_4$, $SiF_3Cl$, $SiF_2Cl_2$, $SiFCl_3$, $GeF_2$, $GeF_4$, $GeF_2Cl_2$, $SnF_2$, $SnF_4$, $PbF_2$, $PbF_4$, and so on; fluorides of Element 15 such as $PF_3$, $PF_5$, $AsF_3$, $AsF_5$, $SbF_3$, $SbF_5$, $SbF_4Cl$, $SbF_3Cl_2$, $SbFCl_3$, $SbFCl_4$, $BiF_3$, $BiF_5$, and so on; fluorides of Element 16 such as $OF_2$, $SF_4$, $SeF_4$, $SeF_6$, $TeF_4$, $TeF_6$, and so on; fluorides of Element 17 such as $F_2$, $ClF$, $ClF_3$, $BrF$, $BrF_3$, $IF_5$, and so on. Among these, the fluorides of the Elements 13~15 are preferable because of product yields, availability, and cost, and $BF_3$, $AlF_3$, $AlF_2Cl$, $SiF_4$, $PF_3$, $PF_5$, $SbF_3$, $SbF_5$, $SbF_4Cl$, and $SbF_3Cl_2$ are preferably exemplified.

Suitable examples of fluorides of the transition elements (transition metal fluorides) include fluorides of Element 3 in the Periodic Table such as $ScF_3$, $YF_3$, $LaF_3$, and so on; fluorides of Element 4 such as $TiF_4$, $ZrF_3$, $ZrF_4$, $HfF_4$, and so on; fluorides of Element 5 such as $VF_3$, $VF_5$, $NbF_5$, $TaF_5$, and so on; fluorides of Element 6 such as $CrF_3$, $MoF_6$, $WF_6$, and so on; fluorides of Element 7 such as $MnF_2$, $MnF_3$, $ReF_6$, and so on; fluorides of Element 8 such as $FeF_3$, $RuF_3$, $RuF_4$, $OsF_4$, $OsF_5$, $OsF_6$, and so on; fluorides of Element 9 such as $CoF_2$, $CoF_3$, $RuF_3$, $IrF_6$, and so on; fluorides of Element 10 such as $NiF_2$, $PdF_2$, $PtF_2$, $PtF_4$, $PtF_6$, and so on; fluorides of Element 11 such as $CuF_2$, $CuFCl$, $AgF$, $AgF_2$, and so on; and fluorides of Element 12 such as $ZnF_2$, $ZnFCl$, $CdF_2$, $HgF_2$, and so on. Among the fluorides of transition elements, the fluorides of Elements 11 (Cu, Ag, Au) and 12 (Zn, Cd, Hg) are exemplified preferably. $ZnF_2$ and $CuF_2$ are furthermore preferable from the viewpoint of practical operation, yield, and cost.

Suitable examples of mixtures or compounds between or among the fluorides of typical elements and/or transition elements include, but are not limited to: $HBF_4$ [a compound of hydrogen fluoride (HF) and $BF_3$], $HPF_6$, $HAsF_6$, $HSbF_6$, LiF/HF [a mixture or salt of lithium fluoride(LiF) and hydrogen fluoride(HF)], NaF/HF, KF/HF, CsF/HF, $(CH_3)_4$NF/HF, $(C_2H_5)_4$NF/HF, $(C_4H_9)_4$NF/HF, $ZnF_2$/HF, $CuF_2$/HF, $BF_3$/HF, $AlF_3$/HF, $SiF_4$/$BF_3$, $SiF_4$/$PF_5$, $SiF_4$/$SbF_5$, $PF_3$/$PF_5$, $AsF_3$/$AsF_5$, $SbF_3$/$SbF_5$, $SbF_3$/$SbF_5$/HF, $ZnF_2$/$SbF_5$, $ZnF_2$/$SbF_5$/HF, $KF$/$SbF_5$, $KF$/$SbF_5$/HF, and so on.

Fluoride source-activating compounds usable in this invention include, but are not limited to, $SbCl_5$, $AlCl_3$, $PCl_5$, $BCl_3$, and other like compounds. Suitable examples of mixtures or compounds of the fluorides with fluoride source-activating compounds include, but are not limited to, $SbF_3$/$SbCl_5$, $BF_3$/$SbCl_5$, $AlF_3$/$SbCl_5$, $SiF_4$/$SbCl_5$, $GeF_4$/$SbCl_5$, $SnF_4$/$SbCl_5$, $PbF_2$/$SbCl_5$, $BiF_3$/$SbCl_5$, $HF$/$SbCl_5$, $ZnF_2$/$SbCl_5$, $CuF_2$/$SbCl_5$, $FeF_3$/$SbCl_5$, $TiF_4$/$SbCl_5$, $SbF_3$/$AlCl_3$, $BF_3$/$AlCl_3$, $AlF_3$/$AlCl_3$, $SiF_4$/$AlCl_3$, $GeF_4$/$AlCl_3$, $SnF_4$/$AlCl_3$, $PbF_2$/$AlCl_3$, $BiF_3$/$AlCl_3$, $HF$/$AlCl_3$, $ZnF_2$/$AlCl_3$, $CuF_2$/$AlCl_3$, $FeF_3$/$AlCl_3$, $TiF_4$/$AlCl_3$, $SbF_3$/$PCl_5$, $BF_3$/$PCl_5$, $AlF_3$/$PCl_5$, $SiF_4$/$PCl_5$, $GeF_4$/$PCl_5$, $SnF_4$/$PCl_5$, $PbF_2$/$PCl_5$, $BiF_3$/$PCl_5$, $HF$/$PCl_5$, $ZnF_2$/$PCl_5$, $CuF_2$/$PCl_5$, $FeF_3$/$PCl_5$, $SbF_3$/$BCl_3$, $BF_3$/$BCl_3$, $AlF_3$/$BCl_3$, $SiF_4$/$BCl_3$, $GeF_4$/$BCl_3$, $SnF_4$/$BCl_3$, $PbF_2$/$BCl_3$, $BiF_3$/$BCl_3$, $HF$/$BCl_3$, $ZnF_2$/$BCl_3$, $CuF_2$/$BCl_3$, and other like compounds combinations. Among these mixtures or compounds of fluorides with fluoride source-activating compounds, mixtures or compounds of fluorides of the Elements 13~15 with fluoride source-activating compounds are preferable from a viewpoint of product yields and cost performance, and among them, $SbF_3$/$SbCl_5$, $AlF_3$/$AlCl_3$, and $PF_3$/$PCl_5$ are more preferable from an additional viewpoint of recovery and recycling of elements such as Sb, Al, and P. The amount used of a fluoride source-activating compound against a fluoride source is from a catalytic amount to any amount that does not hurt the reactions of this invention. The preferable amount of a fluoride source-activating compound against 1 mol of the fluoride source can be selected in the range of from about 0.005 mol to about 1.5 mol, more preferably about 0.01 mol to about 1 mol, furthermore preferably about 0.03 mol to about 0.5 mol, from a viewpoint of cost performance and reaction efficiency and yields.

Among the organic molecules usable for the mixtures, salts, or complexes with the fluorides, pyridines such as pyridine, methylpyridine, dimethylpyridine, trimethylpyridine, and so on, ethers such as dimethyl ether, diethyl ether, dipropyl ether, diisopropyl ether, and so on, alkylamines such as trimethylamine, triethylamine, and so on, nitriles such as acetonitrile, propionitrile, and so on are preferable. Among these, pyridine, dimethyl ether, diethyl ether, triethylamine, and acetonitrile are more preferable because of availability and cost. Suitable examples of mixtures, salts, or complexes of the fluorides with organic molecules include, but are not limited to: $BF_3$ diethyl etherate [$BF_3$. $O(C_2H_5)_2$], $BF_3$ dimethyl etherate, $BF_3$ dibutyl etherate, $BF_3$ tetrahydrofuran complex, $BF_3$ acetonitrile complex ($BF_3$. $NCCH_3$), $HBF_4$ diethyl etherate, HF/pyridine (a mixture of hydrogen fluoride and pyridine), HF/methylpyridine, HF/dimethylpyridine, HF/trimethylpyridine, HF/trimethylamine, HF/triethylamine, HF/dimethyl ether, HF/diethyl ether, and so on. As HF/pyridine, a mixture of about 70 wt % hydrogen fluoride and about 30 wt % pyridine is preferable because of availability.

Among these examples of fluoride sources mentioned above, hydrogen fluoride, fluorides of transition elements in the Periodical Table, fluorides of the Elements 13~15 in the Periodical Table, and mixtures or compounds thereof, as well as mixtures or compounds of these fluorides with fluoride source-activating compounds are preferable. Among these, fluorides of the Elements 13~15 are furthermore preferable for the reactions of Process II. The fluorides of the Elements 13~15 can be preferably used with the fluoride source-activating compounds.

In some embodiments, since the reaction of a (halotetrafluorosulfanyl)aromatic compound with a fluoride source can be slowed down by flowing an inactive gas (such as nitrogen (see Example 2)), it is not preferable that the vapor on the reaction mixture and/or the gas which may be generated from the reaction mixture be removed, for example by flowing an inactive gas on or through the reaction mixture or other methods. This was an unexpected finding discovered by the inventor, as one would not expect removal of the reaction vapor to slow the reaction. Therefore, there may be a case that it is preferable that the reaction of a poly(halotetrafluorosulfanyl)aromatic compound of formula (IV) with a fluoride source be carried out in a closed or sealed reactor, by maintaining the reactor at a constant pressure, or by equipping the reactor with a balloon filled with an inactive gas such as nitrogen, or in any other like manner. In this manner, embodiments of the invention facilitate the presence of the reaction vapor.

Process II can be carried out with or without a solvent. The use of solvent is preferable for mild and efficient reactions. Where a solvent is utilized, alkanes, halocarbons, aromatics, ethers, nitriles, nitro compounds can be used. Example alkanes include normal, branched, cyclic isomers of pentane, hexane, heptane, octane, nonane, decane, dodecane, undecane, and other like compounds. Illustrative halocarbons include dichloromethane, chloroform, carbon tetrachloride, dichloroethane, trichloroethane, terachloroethane, trichlorotrifluoroethane, perfluoropentane, perfluorohexane, perfluorocyclohexane, perfluoroheptane, perfluorooctane, perfluorononane, perfluorodecane, perfluorodecalin, Fluorinert® FC-72, FC-75, FC-77, FC-84, FC-87, FC-104, and FC-40, and other like compounds. Fluorinert® FC series are perfluorinated organic compounds, which are produced by 3M Company. Illustrative aromatics include benzene, toluene, xylene, fluorobenzene, chlorobenzene, dichlorobenzene, trichlorobenzene, hexafluorobenzene, benzotrifluoride, and other like compounds. Illustrative ethers include diethyl ether, dipropyl ether, di(isopropyl)ether, dibutyl ether, dioxane, glyme (1,2-dimethoxyethane), diglyme, triglyme, and other like compounds. Illustrative nitriles include acetonitrile, propionitrile, benzonitrile, and other like compounds. Illustrative nitro compounds include nitromethane, nitroethane, nitrobenzene, and other like compounds. Among them, alkanes and halocarbons are preferable. Where the fluoride source used for the reaction is liquid, it can be used as both a reactant and a solvent. A typical example of this is hydrogen fluoride and a mixture of hydrogen fluoride and pyridine. Hydrogen fluoride and a mixture of hydrogen fluoride and pyridine may be usable as a solvent.

In order to optimize yield with regard to Process II, the reaction temperature is selected in the range of from about −100° C. to about +250° C. More typically, the reaction temperature is selected in the range of from about −80° C. to about +230° C. Most typically, the reaction temperature is selected in the range of from about −80° C. to about +200° C.

In order to obtain economically good yields of the products, the amount of a fluoride source which provides n number of reactive fluoride (employable for the reaction) per molecule can be selected in the range of from about 1/n to about 20/n mol against 1 mol of one unit of $SF_4X$ of a poly(halotetrafluorosulfanyl)aromatic compound (see formula IV). More typically, the amount can be selected in the range of from about 1/n to about 10/n mol from the viewpoint of yield and cost, as less amounts of a fluoride source decrease the yield(s) and additional amounts of a fluoride source do not significantly improve the yield(s).

As described for Process I, the reaction time of Process II also varies dependent on reaction temperature, the substrates, reagents, solvents, and their amounts used. Therefore, one can modify reaction conditions to determine the amount of time necessary for completing the reaction of Process II, but can be from about 1 minute to several days, preferably, within a few days.

Process II is preferably carried out under anhydrous conditions. Anhydrous conditions are preferable because byproducts, compounds having a —$SO_2F$ group(s), are not formed or their formation is suppressed. Hydrous or moist conditions may produce the byproducts depending on the amount of water contained and on the nature of the reagents, solvents, and other reaction conditions. When the product obtained is contaminated with the byproduct(s), the product can be purified by hydrolysis, preferably by alkaline hydrolysis with or without a phase transfer catalyst. The byproducts are hydrolyzed to the corresponding sulfonic acids or sulfonic acid salts which are easily separated from the product.

Process II may also be carried out under hydrous or moist conditions. In some cases, hydrous or moist conditions may accelerate the reaction. Hydrous or moist conditions herein can be prepared in many ways, for example: (1) a hydrous or moist fluoride source mentioned above is used; (2) a moist solvent mentioned above is used; (3) a moist poly(halotetrafluorosulfanyl)aromatic compound (formula IV) is used; (4) an adequate amount of water, steam, or water vapor is added to a fluoride source, a poly(halotetrafluorosulfanyl) aromatic compound (formula IV), solvent, and/or a reaction mixture or a reaction system; (5) moist air is introduced to a fluoride source, a poly(halotetrafluorosulfanyl)aromatic compound (formula IV), solvent, and/or a reaction mixture or a reaction system; and/or (6) the reaction is run in moist air, and so on. When the product obtained is contaminated with byproducts, compounds having a —SO$_2$F group, the product can be purified by hydrolysis, preferably by alkaline hydrolysis with or without a phase transfer catalyst. The byproducts are hydrolyzed to the corresponding sulfonic acids or sulfonic acid salts which are easily separated from the product.

Embodiments of the invention include processes which comprise (see for example Scheme 3, Processes I and II') reacting an aryl sulfur compound having a formula (II) with a halogen selected from the group of chlorine, bromine, iodine, and interhalogens, and a fluoro salt having a formula (III), to form a poly(halotetrafluorosulfanyl)aromatic compound, represented by formula (IV). The poly(halotetrafluorosulfanyl)aromatic compound is then reacted with a fluoride source in the presence of a halogen selected from the group of chlorine, bromine, iodine, and interhalogens to form the poly(pentafluorosulfanyl)aromatic compound as represented by a formula (I).

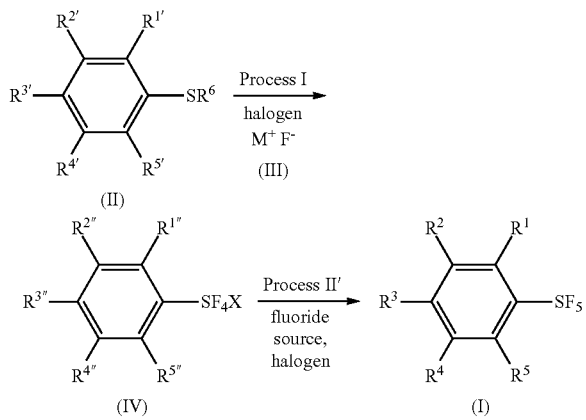

With regard to formulas (I), (II), (III), and (IV), $R^1$, $R^2$, $R^3$, $R^4$, $R^5$, $R^6$, $R^{1'}$, $R^{2'}$, $R^{3'}$, $R^{4'}$, $R^{5'}$, $R^{1''}$, $R^{2''}$, $R^{3''}$, $R^{4''}$, $R^{5''}$, M, and X have the same meaning as defined above.

Process I is as previously described.

Process II' is the same as Process II above, except for the following modifications: the reaction of a poly(halotetrafluorosulfanyl)aromatic compound and a fluoride source is conducted in the presence of a halogen selected from the group of chlorine, bromine, iodine, and interhalogens. Since the reaction of a (halotetrafluorosulfanyl)aromatic compound with a fluoride source is activated in the presence of a halogen as shown in Example 8, it is expected that the reaction of a poly(halotetrafluorosulfanyl)aromatic compound with a fluoride source is activated in the presence of a halogen.

It is expected that a halogen activates a fluoride source and/or prevents disproportionation or reduction of a poly(halotetrafluorosulfanyl)aromatic compound (formula IV), which may occur during this reaction. Therefore, other fluoride source-activating and/or disproportionation or reduction-preventing compounds are within the scope of this invention. The reaction in the presence of a halogen may be carried out by filling a reactor with a halogen gas, adding a halogen to the reaction mixture, dissolving a halogen in the reaction mixture, flowing a halogen gas or vapor into the reaction mixture or the reactor, or others like means. Among the halogens, chlorine (Cl$_2$) is preferable due to ease.

In some cases, during reactions of Process II' which are conducted in the presence of a halogen, halogenation at the aromatic ring of the starting compounds or products may occur dependent on the substrates, reagents, and reaction conditions, forming newly halogenated products. This invention also includes such reactions and newly halogenated products.

The amount of halogen is from a catalytic amount to an amount in large excess. From the viewpoint of cost, a catalytic amount to about 5 mol of the halogen, preferably selected against 1 mol of one unit of SF$_4$X of poly(halotetrafluorosulfanyl)aromatic compound (formula IV).

Embodiments of the present invention include processes which comprise (Process III) reacting an arylsulfur trifluoride having a formula (V) with a halogen (chlorine, bromine, iodine, or interhalogens) and a fluoro salt having a formula (III) to form a poly(halotetrafluorosulfanyl)aromatic compound having a formula (IV) and (Process II) reacting the obtained poly(halotetrafluorosulfanyl)aromatic compound with a fluoride source to form the poly(pentafluorosulfanyl) aromatic compound having a formula (I). Scheme 4 showing Processes III and II are presented as follows:

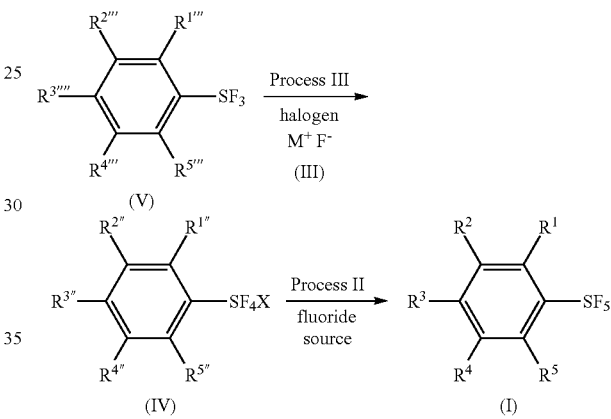

With regard to formulas (I), (III), (IV), and (V), $R^1$, $R^2$, $R^3$, $R^4$, $R^5$, $R^{1''}$, $R^{2''}$, $R^{3''}$, $R^{4''}$, $R^{5''}$, $R^{1'''}$, $R^{2'''}$, $R^{3'''}$, $R^{4'''}$, $R^{5'''}$, M, and X have the same meaning as defined above.

Process III (Scheme 4)

Embodiments of the present invention provide processes for producing a poly(pentafluorosulfanyl)aromatic compound (formula I) by reacting an arylsulfur trifluoride having a formula (V) with a halogen selected from the group of chlorine, bromine, iodine, and interhalogens, and a fluoro salt (formula III) to form a poly(halotetrafluorosulfanyl)aromatic compound having a formula (IV).

Illustrative arylsulfur trifluorides, as represented by formula (V), of the invention can be prepared as described in the literature [see J. Am. Chem. Soc., Vol. 82 (1962), pp. 3064-3072, and J. Fluorine Chem. Vol. 33 (2003), pp. 2505-2509, incorporated herein by reference for all purposes] and are exemplified, but are not limited to, each isomer of benzenedi(sulfur trifluoride) and each isomer of benzenetri(sulfur trifluoride).

Based on consideration of the reaction mechanism, arylsulfur trifluorides (formula V) can be the intermediates in Process I.

A halogen employable in the present invention for Process III is the same as for Process I described above except for the amount used in the reaction.

Fluoro salts having a formula (III) for Process III are the same as for Process I described above, except for the amount used in the reaction.

It is preferable that the reaction of Process III be carried out using a solvent. Examples of suitable solvents are the same as for Process I described above.

In order to obtain economically good yields of the product, the reaction temperature of Process III can be selected in the range of −60° C. ~+70° C. More preferably, the temperature can be selected in the range of −40° C. ~+50° C. Furthermore preferably, the temperature can be selected in the range of −20° C. ~+40° C.

When one of $R^{1'''}$, $R^{2'''}$, $R^{3'''}$, $R^{4'''}$, and $R^{5'''}$ is $SF_3$, about 2 mol to about 10 mol of halogen are combined with about 1 mol of arylsulfur trifluoride (formula V) to obtain a good yield of a poly(halotetrafluorosulfanyl)aromatic compound (formula IV). When two of $R^{1'''}$, $R^{2'''}$, $R^{3'''}$, $R^{4'''}$, and $R^{5'''}$ are $SF_3$, about 3 mol to about 15 mol of halogen are combined with about 1 mol of arylsulfur trifluoride (formula V) to obtain a good economical yield of a poly(halotetrafluorosulfanyl)aromatic compound (formula IV).

The reaction time for Process III is dependent on reaction temperature, the substrates, reagents, solvents, and their amounts used. Therefore, one can choose the time necessary for completing each reaction based on modification of the above parameters, but can be from about 0.5 h to several days, preferably, within a few days.

Process II (Scheme 4)

Process II is as described above.

Embodiments of the present invention include processes which comprise (Process III) reacting an arylsulfur trifluoride having a formula (V) with a halogen (chlorine, bromine, iodine, or interhalogens) and a fluoro salt having a formula (III) to form a poly(halotetrafluorosulfanyl)aromatic compound having a formula (IV), and (Process II') reacting the obtained poly(halotetrafluorosulfanyl)aromatic compound with a fluoride source in the presence of a halogen selected from the group of chlorine, bromine, iodine, and interhalogens to form the poly(pentafluorosulfanyl)aromatic compound having a formula (I). Scheme 5 showing Processes III and II' are as follows: poly(halotetrafluorosuflanyl)aromatic should be poly(halotetrafluorosulfanyl) aromatic;

Scheme 5 (Processes III and II')

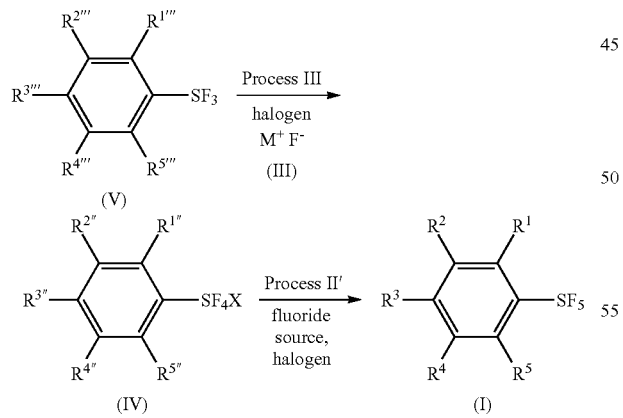

With regard to formulas (I), (III), (IV), and (V), $R^1$, $R^2$, $R^3$, $R^4$, $R^5$, $R^{1''}$, $R^{2''}$, $R^{3''}$, $R^{4''}$, $R^{5''}$, $R^{1'''}$, $R^{2'''}$, $R^{3'''}$, $R^{4'''}$, $R^{5'''}$, M, and X have the same meaning as defined above.

Processes III and II' are as described above.

Furthermore, the present invention includes a process (Scheme 6, Process I) for preparing a poly(halotetrafluorosulfanyl)aromatic compound having a formula (IV), which comprises reacting an aryl sulfur compound having a formula (II) with a halogen selected from the group of chlorine, bromine, iodine, and interhalogens, and a fluoro salt having a formula (III) to form the poly(halotetrafluorosulfanyl)aromatic compound.

Scheme 6 (Process I)

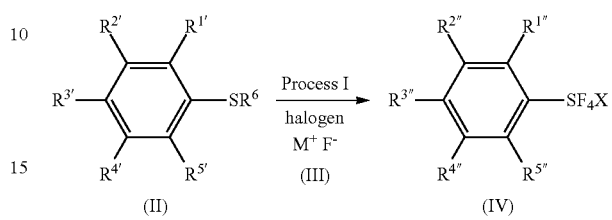

In the formulas (II), (III), and (IV), $R^{1'}$, $R^{2'}$, $R^{3'}$, $R^{4'}$, $R^{5'}$, $R^6$, $R^{1''}$, $R^{2''}$, $R^{3''}$, $R^{4''}$, $R^{5''}$, M, and X represent the same meaning as defined above.

Process I is described above.

Furthermore, the present invention includes a process (Scheme 7, Process III) for preparing a poly(halotetrafluorosulfanyl)aromatic compound having a formula (IV), which comprises reacting an arylsulfur trifluoride having a formula (V) with a halogen selected from the group of chlorine, bromine, iodine, and interhalogens, and a fluoro salt having a formula (III) to form a poly(halotetrafluorosulfanyl)aromatic compound.

Scheme 7 (Process III)

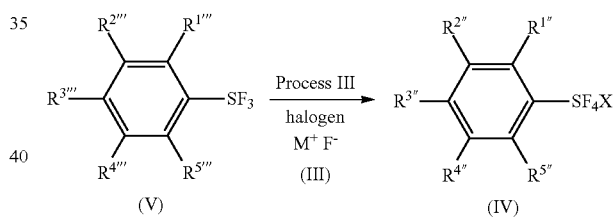

In the formulas (III), (IV), and (V), $R^{1''}$, $R^{2''}$, $R^{3''}$, $R^{4''}$, $R^{5''}$, $R^{1'''}$, $R^{2'''}$, $R^{3'''}$, $R^{4'''}$, $R^{5'''}$, M, and X represent the same meaning as defined above.

Process III is as described above.

Furthermore, the present invention includes a process (Scheme 8, Process II) for preparing a poly(pentafluorosulfanyl)aromatic compound having a formula (I), which comprises reacting a poly(halotetrafluorosulfanyl)aromatic compound having a formula (IV) with a fluoride source to form a poly(pentafluorosulfanyl)aromatic compound.

Scheme 8 (Process II)

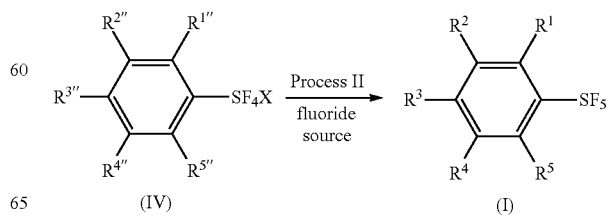

In the formulas (I) and (IV), $R^1$, $R^2$, $R^3$, $R^4$, $R^5$, $R^{1''}$, $R^{2''}$, $R^{3''}$, $R^{4''}$, $R^{5''}$, and X represent the same meaning as defined above.

Process II is as described above.

Furthermore, the present invention includes a process (Scheme 9, Process II') for preparing a poly(pentafluorosulfanyl)aromatic compound having a formula (I), which comprises reacting a poly(halotetrafluorosulfanyl)aromatic compound having a formula (IV) with a fluoride source in the presence of a halogen selected from the group of chlorine, bromine, iodine, and interhalogens to form a poly(pentafluorosulfanyl)aromatic compound.

Scheme 9 (Process II')

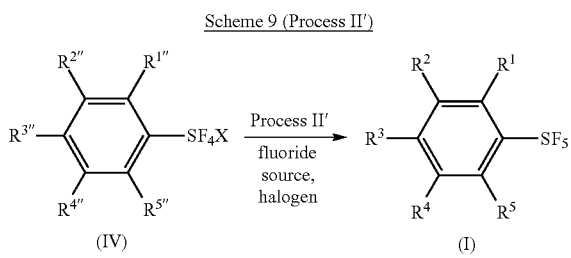

For formulas (I) and (IV), $R^1$, $R^2$, $R^3$, $R^4$, $R^5$, $R^{1''}$, $R^{2''}$, $R^{3''}$, $R^{4''}$, $R^{5''}$, and X represent the same meaning as defined above.

Process II' is as described above.

According to the present invention, the poly(pentafluorosulfanyl)aromatic compounds having the formula (I) can easily and cost-effectively be produced from available starting materials.

Halogenated poly(pentafluorosulfanyl)aromatic compounds as represented by formula (I)($R^2$=Y) among the poly(pentafluorosulfanyl)aromatic compounds of formula (I), are also produced by reacting a hydro poly(pentafluorosulfanyl)aromatic compound having a formula (I)($R^2$=H) with a halogenating agent and an acid to form a poly(pentafluorosulfanyl)aromatic compound of formula (I)($R^2$=Y) (See Scheme 10, Process IV).

Scheme 10 (Process IV)

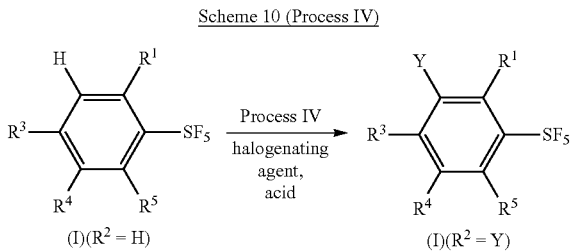

With regard to formulas (I)($R^2$=H) and (I)($R^2$=Y), Y is a halogen atom which is a fluorine atom, chlorine atom, bromine atom, or iodine atom; and one or two of $R^1$, $R^3$, $R^4$, and $R^5$ are a pentafluorosulfanyl ($SF_5$) group and each of the remainders is selected from a group consisting of a hydrogen atom, a halogen atom, a substituted or unsubstituted alkyl group having from 1 to 18 carbon atoms, preferably from 1 to 10 carbon atoms, more preferably from 1 to 4 carbon atoms, a nitro group, and a cyano group.

Process IV requires strong reaction conditions for halogenation because the benzene ring is greatly deactivated by at least two strong electron-withdrawing $SF_5$ groups. Preferable halogenating agents employable for Process IV include: a halogen such as fluorine ($F_2$), chlorine ($Cl_2$), bromine ($Br_2$), and iodine ($I_2$); a N-halo imide such as N-chlorosuccinimide, N-bromosuccinimide, N-iodosuccinimide, 1,3-dibromo-5,5-dimethylhydantoin, and so on; a halogen oxide such as sodium bromate, potassium bromate, sodium iodate, potassium iodate, potassium chlorate, and so on; and mixtures thereof. Preferable acids employable in Process IV include: sulfuric acid, fluorosulfuric acid, chlorosulfuric acid, trifluoromethanesulfonic acid, methanesulfonic acid, trifluoroacetic acid, trichloroacetic acid, and so on, and these aqueous solutions, and mixtures thereof.

Typically, an additional solvent for the reaction of Process IV is not necessary since the acid or its aqueous solution used in Process IV acts as a solvent. When another solvent is needed, water, acetic acid, acetic anhydride, propionic acid, methylene chloride, chloroform, carbon tetrachloride and the like are usable.

In order to optimize yield with regard to Process IV, the reaction temperature can be selected from about −30° C. to about +200° C., preferably, −10° C. to about +170° C., more preferably about 0° C. to about +150° C.

In order to obtain economically good yields of the products using Process IV, the amount of a halogenating agent, which provides n number of reactive halogen atom species (employable for the reaction) per molecule, can be selected in the range of from about 1/n to about 20/n mol against 1 mol of the molecule of formula (I)($R^2$=H). More typically, the amount can be selected in the range of from about 1/n to about 10/n from the viewpoint of yield and cost.

As described above, the reaction time of Process IV varies dependent on reaction temperature, substrates, reagents, solvents, and their amounts used. Therefore, one can modify reaction conditions to determine the amount of time necessary for completing the reaction of Process IV, but can be from about 1 min to several days, preferably, within a few days.

The present invention also provides novel poly(chlorotetrafluorosulfanyl)aromatic compound represented by formula (IV') as useful intermediates for preparing the poly(pentafluorosulfanyl)aromatic compounds of formula (I):

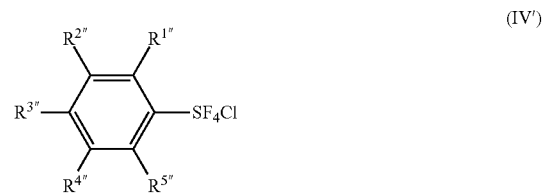

wherein one or two of $R^{1''}$, $R^{2''}$, $R^{3''}$, $R^{4''}$, and $R^{5''}$ are $SF_4Cl$ and each of the remainders is a hydrogen atom, a halogen atom, a substituted or unsubstituted alkyl group having 1 to 18 carbon atoms, preferably 1 to 10 carbon atoms, more preferably 1 to 4 carbon atoms, a nitro group, or a cyano group. The remainders are preferably selected from a group consisting of a hydrogen atom and a halogen atom. The halogen atom can be a fluorine atom, a chlorine atom, a bromine atom, or an iodine atom.

Among these, 1,2-, 1,3-, and 1,4-bis(chlorotetrafluorosulfanyl)benzene, 1,3-bis(chlorotetrafluorosulfanyl)-5-fluoro-, -chloro-, -bromo-, and -iodo-benzene, 1,4-bis(chlorotetrafluorosulfanyl)-2,5-difluorobenzene, 1,4-bis(chlorotetrafluorosulfanyl)-2,3,5,6-tetrafluorobenzene, 1,2,3-, 1,2,4-, and 1,3,5-tris(chlorotetrafluorosulfanyl)benzene, and 1,3,5-trifluoro-2,4,6-tris(chlorotetrafluorosulfanyl)benzene are preferable. 1,3- and 1,4-Bis(chlorotetrafluorosulfanyl)benzene, 1,3-bis(chloroterafluorosulfanyl)-5-bromobenzene, 1,4-bis(chlorotetrafluorosulfanyl)-2,5-difluorobenzene, 1,4-bis(chlorotetrafluorosulfanyl)-2,3,5,6-tetrafluorobenzene, and 1,3,5-tris(chlorotetrafluorosulfanyl)benzene are more preferable.

The present invention also provides a novel and useful bis(pentafluorosulfanyl)benzene compound represented by formula (I″);

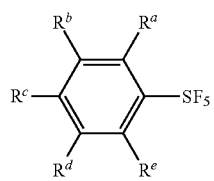

(I″)

wherein one of $R^a$, $R^b$, $R^c$, $R^d$, and $R^e$ is a $SF_5$ group and each of the remainders is selected from a group consisting of a hydrogen atom and a halogen atom. The halogen atom can be a fluorine atom, a chlorine atom, a bromine atom, or an iodine atom.

Among these, 1,2-bis(pentafluorosulfanyl)benzene, 1,3-bis(pentafluorosulfanyl)benzene, 1,4-bis(pentafluorosulfanyl)benzene, 1,3-bis(pentafluorosulfanyl)-5-fluoro-, -chloro-, -bromo-, and -iodo-benzene, 1,4-bis(pentafluorosulfanyl)-2,5-difluorobenzene, and 1,4-bis(pentafluorosulfanyl)-2,3,5,6-tetrafluorobenzene are preferable. 1,3-Bis(pentafluorosulfanyl)benzene, 1,4-bis(pentafluorosulfanyl)benzene, 1,3-bis(pentafluorosulfanyl)-5-bromobenzene, 1,4-bis(pentafluorosulfanyl)-2,5-difluorobenzene, and 1,4-bis(pentafluorosulfanyl)-2,3,5,6-tetrafluorobenzene are more preferable.

The following examples will illustrate the present invention in more detail, but it should be understood that the present invention is not deemed to be limited thereto.

EXAMPLES

The following examples are provided for illustrative purposes only and are not intended to limit the scope of the invention. Tables 2 and 3 provide structure names and formulas for reference when reviewing the following examples:

TABLE 2

Poly(pentafluorosulfanyl)aromatic compounds (Formulas Ia-f)

| Formula Number | Name | Structure |
|---|---|---|
| Ia | 1,3-Bis(pentafluorosulfanyl)benzene | |
| Ib | 1,3-Bis(pentafluorosulfanyl)-5-bromobenzene | |
| Ic | 1,4-Bis(pentafluorosulfanyl)benzene | 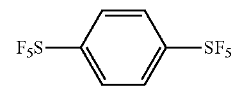 |
| Id | 1,4-Bis(pentafluorosulfanyl)-2,5-difluorobenzene | 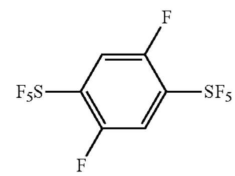 |
| Ie | 1,4-Bis(pentafluorosulfanyl)-2,3,5,6-tetrafluorobenzene | 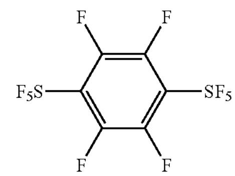 |
| If | 1,3,5-Tris(pentafluorosulfanyl)benzene | 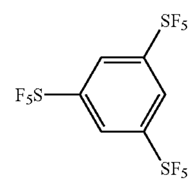 |

TABLE 3

Poly(halotetrafluorosulfanyl)aromatic compounds (Formulas IVa-f)

| Formula Number | Name | Structure |
|---|---|---|
| IVa | 1,3-Bis(chlorotetrafluorosulfanyl)benzene | 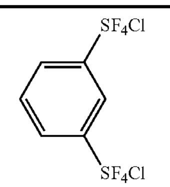 |
| IVb | 1,3-Bis(chlorotetrafluorosulfanyl)-5-bromobenzene | 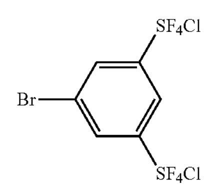 |
| IVc | 1,4-Bis(chlorotetrafluorosulfanyl)benzene | 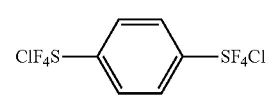 |
| IVd | 1,4-Bis(chlorotetrafluorosulfanyl)-2,5-difluorobenzene | 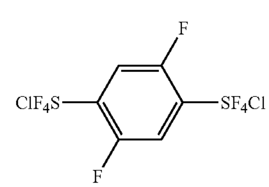 |

TABLE 3-continued

Poly(halotetrafluorosulfanyl)aromatic compounds (Formulas IVa-f)

| Formula Number | Name | Structure |
|---|---|---|
| IVe | 1,4-Bis(chlorotetrafluoro-sulfanyl)-2,3,5,6-tetrafluoro-benzene | ClF$_4$S—(C$_6$F$_4$)—SF$_4$Cl |
| IVf | 1,3,5-Tris(chlorotetrafluoro-sulfanyl)benzene | 1,3,5-(ClF$_4$S)$_3$C$_6$H$_3$ |

Example 1

Synthesis of 1,3-bis(pentafluorosulfanyl)benzene(Ia) from 1,3-benzenedithiol

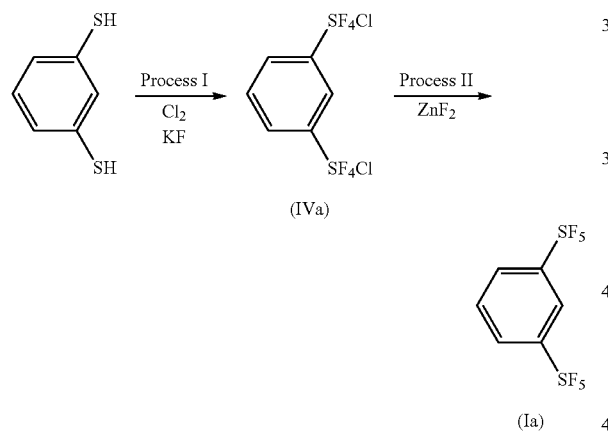

(Process I) A 500 mL fluoropolymer (PFA) reactor was setup with magnetic stirrer, ice bath, gas (N$_2$, Cl$_2$) inlet tube, and gas outlet tube protected by a CaCl$_2$ tube. Gas flow was controlled by digital controller and measured by digital integrator. The vessel was charged with anhydrous potassium fluoride (100 g, 1.72 mol), and set up for reaction under nitrogen flow. Anhydrous acetonitrile (300 mL) was added, followed by 1,3-benzenedithiol (9.78 g, 68.7 mmol). After chilling in the ice bath with stirring under N$_2$ flow for 1 hour, N$_2$ was stopped and then chlorine gas was introduced below the surface at 60-80 mL/min with vigorous stirring. Over approximately 6 hours, a total of 27.11 L (1.21 mol) of Cl$_2$ was added. The reaction was then allowed to come to room temperature with stirring. After allowing to stir and react for two days, the reaction mixture was filtered, washed through with dry acetonitrile (200 mL). The solvent was then removed at room temperature under vacuum, leaving the crude product (23.2 g, crude yield 93%) as a white solid, which was recrystallized from pentane in a freezer to give white crystals of 1,3-bis(chlorotetrafluorosulfanyl)benzene (IVa) (14.08 g, yield 56%). To obtain a sample for analysis, some of the crystals were further recrystallized. The properties and spectral data of 1,3-bis(chlorotetrafluorosulfanyl)benzene (IVa) are shown in the following: m.p. 82-83.5° C. (in a sealed capillary); $^{19}$F NMR (CDCl$_3$) δ 136.14 (s, SF$_4$Cl); $^1$H NMR (CDCl$_3$) δ 8.12 (t, J=2.0 Hz, 1H, 2-H), 7.89 (dd, J=8.3, 2.0 Hz, 2H,4,6-H), 7.58 (t, J=8.3 Hz, 1H, 5-H); $^{13}$C NMR (CDCl$_3$) δ 155.12 (quintet, J=20.6 Hz), 129.25 (s), 129.04 (t, J=4.3 Hz), 124.12 (quintet, J=4.9 Hz). Elemental analysis; calcd for C$_6$H$_4$Cl$_2$F$_8$S$_2$; C, 19.85%, H, 1.11%. Found, C, 20.30%, H, 1.20%. The NMR showed that 1,3-bis(chlorotetrafluorosulfanyl)benzene obtained is a trans,trans-isomer.

(Process II) A 130 mL fluoropolymer (PFA) reactor was set up with magnetic stirrer, oil bath, gas (N$_2$) inlet tube, outlet port and water condenser. The vessel was charged with anhydrous ZnF$_2$ (6.33 g, 61.2 mmol) and 1,3-bis(chlorotetrafluorosulfanyl)benzene (IVa) (10.02 g, 27.6 mmol) prepared in Process I, and set up for reaction. After a N$_2$ purge, the set up was capped with a balloon (the water condenser was connected to a balloon) and the reactor was heated to 140° C. for 17 hours. The reaction mixture was then cooled to room temperature and extracted with pentane. The pentane solution was filtered and removal of the solvent gave a solid (8.25 g). The $^{19}$F NMR analysis of the solid showed that 1,3-bis(pentafluorosulfanyl)benzene (Ia) is produced in 54% yield from the starting material (IVa). The pure product was obtained as white crystals by recrystallization from pentane in a freezer. The properties and spectral data of 1,3-bis(pentafluorosulfanyl)benzene (Ia) are shown in the following: m.p. 62-62.8° C. (in a sealed capillary); $^{19}$F NMR (CDCl$_3$) δ 81.88 (quintet, J=150.4 Hz, 2F, 2×SF), 62.95 (d, J=150.4 Hz, 8F, 2×SF$_4$); $^1$H NMR (CDCl$_3$) δ 8.16 (t, J=2.0 Hz, 1H, 2-H), 7.93 (dd, J=8.2, 2.0 Hz, 2H,4,6-H), 7.63 (t, J=8.2 Hz, 1H, 5-H); $^{13}$C NMR (CDCl$_3$) δ153.72 (quintet, J=19.1 Hz), 129.49 (s), 129.25 (t, J=4.7 Hz), 124.34 (m); GC-Mass m/z 330 (M$^+$). Elemental analysis; calcd for C$_6$H$_4$F$_{10}$S$_2$; C, 21.82%, H, 1.22%. Found, C, 21.79%, H, 1.52%.

Examples 2-5

Synthesis of poly(pentafluorosulfanyl)aromatic compounds (Ic)~(If) from the corresponding aryl sulfur compounds (Process I) An aryl sulfur compound of formula (II) was reacted with chlorine and potassium fluoride in acetonitrile in a similar way as in Process I of Example 1. Table 4 shows the amounts of the aryl sulfur compounds, reagents, and solvents, reaction conditions, and results for Examples 2-5 together with those of Example 1. Properties and spectral data of the products, poly(halotetrafluorosulfanyl)aromatic compounds (IVc)-(IVf) are shown below.

Regarding the chemical structure of SF$_4$Cl of the products (IVc)-(IVf) obtained from Process I: $^{19}$F NMR analysis showed that reaction in Example 2 gave product (IVc) having a trans conformation at SF$_4$Cl. Reaction in Example 3 gave products (IVd) having trans and cis conformation in which a ratio of trans:cis is 93:7. Reaction in Example 4 gave products (IVe) having trans and cis conformation in which a ratio of trans:cis is 57:43. Reaction in Example 5 gave product (IVf) having a trans conformation.

Regarding post-treatment of Process I: for Example 2, the reaction mixture was filtered and washed through with dry dichloromethane. The filtrate was dried by vacuum to give 17.2 g (yield 74%) of product (IVc) (trans,trans-isomer), which was washed with dry dichloromethane to give an analytical sample of IVc. For Example 3, the reaction mixture was filtered and washed through with dry acetonitrile then chloroform. The filtrate was dried by vacuum to give a white solid, which was washed with a small amount of dry dichloromethane to give 13.2 g (yield 52%) of IVd, which was mostly a trans,trans-isomer (trans/cis=96/4). For Example 4, the reaction mixture was filtered and washed through with dry chloroform. The filtrate was dried by vacuum to give a white solid. The solid was recrystallized from a 1:1 mixture of dry dichloromethane and pentane and filtered to give 6.76 g of pure IVe, which was a mixture of trans,trans- and cis,cis-isomers (trans/cis=80/20). By repeated recrystallization of the solid obtained from the filtrate, additional 15.25 g was obtained. The total amount of IVe was 22.0 g (yield 79%). For Example 5, the reaction mixture was filtered and washed through dry acetonitrile then dichloromethane. The filtrate was dried by vacuum to give a white solid, which was recrystallized from a mixture of dichloromethane and pentane to give 10.55 g (crude yield 84%) of crude product IVf, which was purified by recrystallization from pentane.

(Process II) A fluoropolymer (PFA) vessel was charged with 9.89 g (27.2 mmol) of IVc obtained from Process 1 and 320 mL of Fluorinert® FC-72 (perfluorinated organic compounds having b.p. 56° C., available from SynQuest laboratories, Inc.) under nitrogen atmosphere and the mixture was cooled on a bath of around −80° C. A solution of 2.10 mL (30 mmol) of $SbF_5$ in 35 mL of FC-72 was added into the stirred mixture and the mixture was allowed to warm gradually to room temperature over about 8 h. After stirring overnight at room temperature, the reaction mixture was filtered and treated with KF, then filtered. The solvent was removed by reduced pressure and the residue was recrystallized from FC-72 to give 5.83 g (65%) of product Ic. A pure sample of Ic was obtained by washing with FC-72 thoroughly.

Products Id, Ie, and If were prepared in a similar way as in Process II above used in the preparation of Ic. Table 4 shows the amounts of the starting materials IVd-f, reagents, and solvents, reaction conditions, and results of Examples 2-5. Properties and spectral data of the products (Ic)-(If) are shown below.

Regarding post-treatment of Process II: for Example 2, it was described above. For Example 3, the reaction mixture was filtered and treated with KF, then filtered. The solvent was removed under reduced pressure and the residue was crystallized from pentane to give 5.27 g (52%) of product Id. For Example 4, the reaction mixture was filtered and treated with KF, then filtered. The filtrate was concentrated to give crystals (3.36 g, yield 67%) of product Ie. For Example 5, the reaction mixture was filtered and treated with KF, then filtered. The filtrate was dried up to give 0.87 g of product If. The solid obtained from the reaction mixture was quenched with KF and extracted with FC-72 to give an additional 1.1 g, which was found to be about 0.48 g of the product by GC analysis. The total yield was about 1.35 g (36%).

TABLE 4

Synthesis of poly(pentafluorosulfanyl)aromatic compounds (Ia), (Ic)-(If) from the corresponding aryl sulfur compounds (II)

| | | Process I | | | | | | | Process II | | |
|---|---|---|---|---|---|---|---|---|---|---|---|
| Ex. | (II) | Halogen | (III) | Solvent | Conditions | (IV) | Yield | Amount of (IV) | Fluoride source | Solv. | Conditions | (I) | Yield |
| 1 | 1,3-(HS)₂C₆H₄, 9.78 g (68.7 mmol) | Cl₂ 1.21 mol | KF 100 g (1.72 mol) | CH₃CN 300 mL | ice bath 6 h and r.t. 2 days | IVa 1,3-(ClSF₄)₂C₆H₄, 14.08 g | 56% | 10.02 g (27.6 mmol) | ZnF₂ 6.33 g (61.2 mmol) | non | 140° C. 17 h | Ia 1,3-(SF₅)₂C₆H₄ | 54% |
| 2 | 1,4-(HS)₂C₆H₄, 9.10 g (64 mmol) | Cl₂ 1.26 mol | KF 100 g (1.72 mol) | CH₃CN 400 mL | ice bath 6 h and r.t. 2 days | IVc 1,4-(ClSF₄)₂C₆H₄, 17.2 g | 74% | 9.89 g (27.2 mmol) | SbF₅ 8.47 g (82 mmol) in 35 mL of FC-72 | FC-72 320 mL | ~−80° C. for 8 h and r.t., overnight → r.t. | Ic 1,4-(SF₅)₂C₆H₄ 5.83 g | 65% |
| 3 | 2,5-F₂-1,4-(HS)₂C₆H₂, 11.3 g (63 mmol) | Cl₂ 1.27 mol | KF 102 g (1.75 mol) | CH₃CN 450 mL | ice bath 7 h and r.t. overnight | IVd 2,5-F₂-1,4-(ClSF₄)₂C₆H₂, 13.2 g | 52% | 11.1 g (27.8 mmol) | SbF₅ 2.20 mL (30.7 mmol) in 40 mL of FC-72 | FC-72 350 mL | ~−80° C. for 8 h and r.t., overnight → r.t. | Id 2,5-F₂-1,4-(SF₅)₂C₆H₂ 5.27 g | 52% |
| 4 | 2,3,5,6-F₄-1,4-(HS)₂C₆, 13.6 g (64 mmol) | Cl₂ 1.30 mol | KF 102 g (1.75 mol) | CH₃CN 500 mL | ice bath 7 h and r.t. overnight | IVe 2,3,5,6-F₄-1,4-(ClSF₄)₂C₆, 22.0 g | 79% | 5.41 g (12.4 mmol) | SbF₅ 3.12 g (14.4 mmol) in 50 mL of FC-72 | FC-72 20 mL | r.t. overnight | Ie 2,3,5,6-F₄-1,4-(SF₅)₂C₆ 3.36 g | 67% |

TABLE 4-continued

Synthesis of poly(pentafluorosulfanyl)aromatic compounds (Ia), (Ic)–(If) from the corresponding aryl sulfur compounds (II)

| | | Process I | | | | | Process II | | |
|---|---|---|---|---|---|---|---|---|---|
| Ex. | (II) | Halogen | (III) | Solvent | Conditions | (IV) | Yield | Amount of (IV) | Fluoride source | Solv. | Conditions | (I) | Yield |
| 5 |  4.34 g (25 mmol) | Cl$_2$ 0.85 mol | KF 65 g (1.12 mol) | CH$_3$CN 400 mL | ice bath 4 h and r.t. overnight | 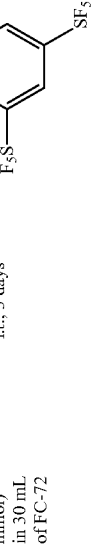 IVf 10.55 g | 84% | 4.12 g (8.2 mmol) | SbF$_5$ 1.25 mL (17.8 mmol) in 30 mL of FC-72 | FC-72 400 mL | ice bath → r.t. for ~6 h and r.t., 3 days |  If 1.35 g | 36% |

Properties and spectral data of the products (IVa) and (Ia) are as shown in Example 1. Properties and spectral data of products (IVc)-(IVf) and (Ic)-(If) are shown in the following:

1,4-Bis(chlorotetrafluorosulfanyl)benzene (IVc); m.p. 200.8-201.6° C.; $^{19}$F NMR (CDCl$_3$) δ 135.72 (s, 8F); $^1$H NMR (CDCl$_3$) δ 7.84 (s, 4H); $^{13}$C NMR (CDCl$_3$) δ 156.90 (quintet, J=20.2 Hz), 126.73 (m); GC-Mass m/z 330 (M$^+$). Elemental analysis; calcd for C$_6$H$_4$Cl$_2$F$_8$S$_2$; C, 19.85%, H, 1.11%. Found, C, 19.71%, H, 1.10%. NMR analysis showed that product (IVc) obtained is a trans,trans-isomer.

1,4-Bis(pentafluorosulfanyl)benzene (Ic); m.p. 108.8-109.7° C.; $^{19}$F NMR (CDCl$_3$) δ 80.6-82.7 (m, 2F), 62.55 (d, J=149.9 Hz, 8F); $^1$H NMR (CDCl$_3$) δ 7.88 (s, 4H); $^{13}$C NMR (CDCl$_3$) δ 155.53 (quintet, J=19.0 Hz), 126.91 (m); GC-Mass m/z 330 (M$^+$). Elemental analysis; calcd for C$_6$H$_4$F$_{10}$S$_2$; C, 21.82%, H, 1.22%. Found, C, 21.59%, H, 1.23%.

1,4-Bis(chlorotetrafluorosulfanyl)-2,5-difluorobenzene (IVd); m.p. 161.5-162.9° C. (a 96:4 mixture of trans and cis conformation); $^{19}$F NMR (CDCl$_3$) (a 96:4 mixture of trans and cis conformation) δ 155.63 (m, cis-SF), 138.52 (m, trans-SF$_4$), 112.95 (m, cis-SF$_2$), 71.37 (m, cis-SF), −109.25 (m, CF); $^1$H NMR (CDCl$_3$) (a 96:4 mixture of trans and cis conformation) δ 7.63 (m, 2H); $^{13}$C NMR (CDCl$_3$) (a 96:4 mixture of trans and cis conformation) δ 150.75 (d, J=263.3 Hz), 143.94 (m), 118.50 (m). Elemental analysis (a 96:4 mixture of trans and cis conformation); calcd for C$_6$H$_2$Cl$_2$F$_{10}$S$_2$; C, 18.06%, H, 0.51%. Found, C, 18.01%, H, 0.51%.

1,4-Bis(pentafluorosulfanyl)-2,5-difluorobenzene (Id); m.p. 73.0-74.6° C.; $^{19}$F NMR (CDCl$_3$) δ 76.3-78.5 (m, 2F), 67.71 (dd, J=152.3, 24.8 Hz, 8F), −109.77 (m, 2F); $^1$H NMR (CDCl$_3$) δ 7.67 (m, 2H); $^{13}$C NMR (CDCl$_3$) δ 151.07 (d, J=262.3 Hz), 142.76 (m), 118.54 (dm, J=26.0 Hz); GC-Mass m/z 366 (M$^+$). Elemental analysis; calcd for C$_6$H$_2$F$_{12}$S$_2$; C, 19.68%, H, 0.55%. Found, C, 19.33%, H, 0.58%.

1,4-Bis(chlorotetrafluorosulfanyl)-2,3,5,6-tetrafluorobenzene (IVe); m.p. 135-141° C. (a 80:20 mixture of trans and cis conformation); $^{19}$F NMR (CDCl$_3$) (a 62:38 mixture of trans and cis conformation) δ 148.6-150.4 (m, cis-SF), 142.22 (m, trans-SF$_4$), 122.9~124.2 (m, cis-SF$_2$), 77.7~79.2 (m, cis-SF), −129.2~−130.3 (m, CF, trans and cis); $^{13}$C NMR (CDCl$_3$) (a 62:38 mixture of trans- and cis-conformation) δ 143.7-144.7 (m), 140.2-141.2 (m), 134.5 (m). Elemental analysis (a 80:20 mixture of trans and cis conformation); calcd for C$_6$Cl$_2$F$_{12}$S$_2$; C, 16.56%, H, 0.00%. Found, C, 16.54%, H, <0.05%.

1,4-Bis(pentafluorosulfanyl)-2,3,5,6-tetrafluorobenzene (Ie); m.p. 129.2-130.0° C.; $^{19}$F NMR (CDCl$_3$) δ 71.0-74.4 (m, 10F), −130.8 (m, 4F); $^{13}$C NMR (CDCl$_3$) δ 144.9 (m), 141.3 (m), 133.3 (m); GC-Mass m/z 402 (M$^+$). Elemental analysis; calcd for C$_6$F$_{14}$S$_2$; C, 17.92%, H, 0.00%. Found, C, 17.99%, H, <0.05%.

1,3,5-Tris(chlorotetrafluorosulfanyl)benzene (IVf); $^{19}$F NMR (CDCl$_3$) δ 135.32 (s); $^1$H NMR (CDCl$_3$) δ 8.24 (s); $^{13}$C NMR (CDCl$_3$) δ 127.01 (m), 154.96 (quintet, J=22.9 Hz). NMR analysis showed that product (IVf) obtained is a trans,trans,trans-isomer.

1,3,5-Tris(pentafluorosulfanyl)benzene (If); m.p. 132.8-133.5° C.; $^{19}$F NMR (CDCl$_3$) δ 63.31 (dm, J=151.8 Hz, 12F), 78.3-80.5 (m, 3F); $^1$H NMR (CDCl$_3$) δ 8.31 (s); $^{13}$C NMR (CDCl$_3$) δ 153.65 (quintet, J=21.3 Hz), 127.31 (m); GC-Mass m/z 456 (M$^+$). Elemental analysis; calcd for C$_6$H$_3$F$_{15}$S$_3$; C, 15.79%, H, 0.66%. Found, C, 15.48%, H, 0.62%.

Example 6

Preparation of 1,3-bis(chlorotetrafluorosulfanyl)-5-bromobenzene (IVb)

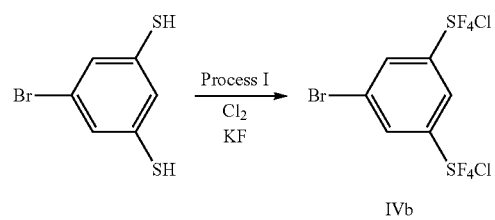

(Process I) A 240 mL fluoropolymer (PFA) reactor was set up with magnetic stirrer, ice bath, gas (N$_2$, Cl$_2$) inlet tube, and gas outlet tube protected by a CaCl$_2$ tube. Gas flow was controlled by digital controller and measured by digital integrator. The reactor was charged with anhydrous potassium fluoride (30 g, 0.51 mol) and 5-bromo-1,3-benzenedithiol (2.97 g, 13.4 mmol), and set up for reaction under nitrogen flow. Anhydrous acetonitrile (120 mL) was added, and the slurry was stirred at ambient temperature for about 1 hour, after which stirring was continued for about 1 hour on an ice bath. N$_2$ was stopped and then chlorine gas was introduced below the surface at about 30 mL/min with vigorous stirring. For approximately 4 hours, a total of 7.91 L (0.35 mol) of Cl$_2$ was added. The reaction mixture was then allowed to come to room temperature overnight with stirring. The reaction mixture was purged with nitrogen, then suction filtered, washing through with acetonitrile. A small amount of potassium fluoride was added to the reaction solution, and the solvents were then removed at ambient temperature under approximately 4 mmHg vacuum, leaving a white solid. A small amount of dry dichloromethane was added to dissolve the product, which was then filtered to remove potassium fluoride and other insolubles. Removal of dichloromethane under vacuum yielded crude product (5.39 g, crude yield 91%) as a white powder. Recrystallization from pentane in a freezer yielded 4.16 g (yield 65%) of 1,3-bis(chlorotetrafluorosulfanyl)-5-bromobenzene; m.p. 146.1-148° C. (with decomposition); $^{19}$F NMR δ (CDCl$_3$) 135.8 ppm (s); $^1$H NMR δ (CDCl$_3$) 8.05 (m, 1H), 8.02 (m, 2H); $^{13}$C NMR δ (CDCl$_3$) 155.58 (quintet, J=21.7 Hz, C-1,3), 132.20 (m, C-4,6), 122.79 (m, C-2), 122.29 (s, C-5). NMR analysis showed that 1,3-bis(chlorotetrafluorosulfanyl)-5-bromobenzene obtained is a trans,trans-isomer.

Example 7

Preparation of 1,3-bis(pentafluorosulfanyl)-5-bromobenzene (Ib)

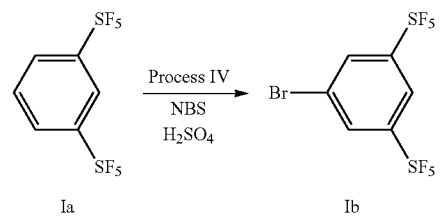

A 30 mL capped fluoropolymer (PFA) reactor with a single port and stopcock was charged with 1,3-bis(pentafluorosulfanyl)benzene (Ia) (1.65 g, 5 mmol), N-bromosuccinimide (NBS) (3.4 g, 19 mmol), and concentrated sulfuric acid (6 mL). The stopcock was closed to seal the reaction and the mixture was heated on an oil bath at 60-65° C. with magnetic stirring for 22 hours. After cooling, the reaction mixture was quenched into a mixture of dilute aqueous sodium carbonate solution and chloroform. After separation, the aqueous phase was extracted with chloroform, the combined organic extract was dried over magnesium sulfate and filtered. The filtrate was evaporated up to dryness to give a solid, which was a 71:29 mixture of 1,3-bis(pentafluorosulfanyl)-5-bromobenzene and 1,3-bis(pentafluorosulfanyl)benzene by GC analysis. The mixture was column-chromatographed on silica gel using hexane as an eluent to give pure 1,3-bis(pentafluorosulfanyl)-5-bromobenzene (Ib) (about 64% yield): m.p. 65.9~66.4° C. (in a sealed capillary); $^{19}$F NMR δ (CDCl$_3$) 79.4-81.6 (m, 2F), 62.9-63.6 (m, 8F); $^1$H NMR δ (CDCl$_3$) 8.05-8.10 (m); $^{13}$C NMR δ (CDCl$_3$) 154.17 (p, J=20.2 Hz), 132.41 (t, J=4.3 Hz), 122.98 (p, J=5.1, 4.3 Hz), 122.53 (s); GC-Mass m/z 410(M$^+$), 408 (M$^+$). Elemental analysis; calcd for C$_6$H$_3$BrF$_{10}$S$_2$; C, 17.62%, H, 0.74%. Found, C, 17.61%, H, 0.73%.

Example 8

Reactions of (Chlorotetrafluorosulfanyl)Benzene (PhSF$_4$Cl) and ZnF$_2$ Under No Flow, Slow and Fast Flows of an Inactive as (Nitrogen), and Flow of Halogen (Cl$_2$)

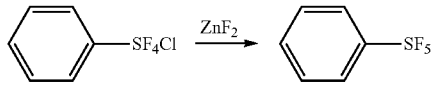

Run 1; no flow of N$_2$
Run 2; slow flow of N$_2$
Run 3; fast flow of N$_2$
Run 4; flow of Cl$_2$ Run 1 with a Balloon Filled with N$_2$ (No Flow of N$_2$)

In a dry box, a reaction vessel made of fluoropolymer was charged with 1.0 g (4.54 mmol) of trans-(chlorotetrafluorosulfanyl)benzene (trans-PhSF$_4$Cl) and 0.28 g (2.7 mmol) of anhydrous ZnF$_2$. The reaction vessel was removed from the dry box and equipped with a balloon filled with N$_2$. The reaction mixture was stirred at 120° C. for 4 hours. The reaction mixture was analyzed by $^{19}$F NMR, results are shown in Table 5.

Run 2 with N$_2$ Flow of a Rate of 5.4 Ml/Min (Slow Flow of N$_2$)

In a dry box, a 50 mL reaction vessel made of fluoropolymer was charged with 10.0 g (0.045 mol) of trans-PhSF$_4$Cl and 2.8 g (0.027 mol) of anhydrous ZnF$_2$. The reaction vessel was removed from the dry box, and equipped with a condenser made of fluoropolymer and connected to a N$_2$ gas flowing device. The reaction mixture was slowly heated to 120° C. with N$_2$ flowing at the rate of 5.4 mL/minute. The reaction mixture was stirred at 120° C. with N$_2$ flowing for 5 hours. After being cooled to room temperature, the reaction mixture was analyzed with $^{19}$F NMR. The results are shown in Table 5.

Run 3 with N$_2$ Flow of a Rate of 26.9 Ml/Min (Fast Flow of N$_2$)

In a dry box, a 50 mL reaction vessel made of fluoropolymer was charged with 10.0 g (0.045 mol) of trans-PhSF$_4$Cl and 2.8 g (0.027 mol) of anhydrous ZnF$_2$. The reaction vessel was removed from the dry box, and equipped with a condenser made of fluoropolymer and connected to a N$_2$ gas flowing device. The reaction mixture was slowly heated to 120° C. with N$_2$ flowing at a rate of 26.9 mL/minute. The reaction mixture was stirred at 120° C. with N$_2$ flowing for 5 hours. After being cooled to room temperature, the reaction mixture was analyzed with $^{19}$F NMR. The results are shown in Table 5.

Run 4 with Cl$_2$ Flow of a Rate of 4.6 Ml/Min (Flow of Halogen):

In a dry box, a 50 mL reaction vessel made of fluoropolymer was charged with 10.0 g (0.045 mol) of trans-PhSF$_4$Cl and 2.8 g (0.027 mol) of anhydrous ZnF$_2$. The reaction vessel was removed from the dry box, and equipped with a condenser made of fluoropolymer and connected to a Cl$_2$ gas flowing device. The reaction mixture was slowly heated to 120° C. with Cl$_2$ flowing at a rate of 4.6 mL/minute. The reaction mixture was stirred at 120° C. with Cl$_2$ flowing. The progress of the reaction was monitored by $^{19}$F NMR. After 40 minutes at 120° C., three major compounds (trans-PhSF$_4$Cl, cis-PhSF$_4$Cl, and PhSF$_5$) were detected to be present in the reaction mixture. The mol ratio of trans-PhSF$_4$Cl:cis-PhSF$_4$Cl:PhSF$_5$ was 0.5:3.3:100. After additional 60 minutes at 120° C., trans- and cis-PhSF$_4$Cl disappeared and only PhSF$_5$ was detected by $^{19}$F NMR. The reaction was completed within 1.7 h at 120° C. The NMR analysis showed that PhSF$_5$ was produced in 92% yield. This result is shown in Table 5. This experiment showed that the reaction is greatly accelerated by the presence of chlorine and the product is obtained in a high yield. This experiment also showed that cis-PhSF$_4$Cl is formed intermediately by the isomerization of trans-PhSF$_4$Cl; the cis-PhSF$_4$Cl is converted to the product, PhSF$_5$.

TABLE 5

Reactions of (chlorotetrafluorosulfanyl)benzene with ZnF$_2$ with or without flow of N$_2$ or Cl$_2$

| Run | N$_2$ or Cl$_2$ flow | Reaction time | Molar ratio of PhSF$_5$:PhSF$_4$Cl* | Yield of PhSF$_5$ |
|---|---|---|---|---|
| Run 1 | no flow | 4 hours | PhSF$_4$Cl was consumed | 88% |
| Run 2 | N$_2$; 5.4 mL/min | 5 hours | 1:0.35 | 67% |
| Run 3 | N$_2$; 26.9 mL/min | 5 hours | 1:1.39 | 38% |
| Run 4 | Cl$_2$; 4.6 mL/min | 1.7 hours | PhSF$_4$Cl was consumed | 92% |

*PhSF$_5$ = (pentafluorosulfanyl)benzene. PhSF$_4$Cl; a mixture of trans- and cis-isomers.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:
1. A process for preparing a poly(pentafluorosulfanyl)aromatic compound having a formula (I) as follows:

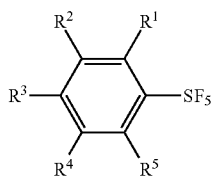

(I)

the process comprising:
reacting an aryl sulfur compound having a formula (II):

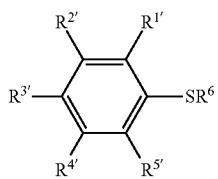

(II)

with a halogen selected from the group consisting of chlorine, bromine, iodine, and interhalogens, and a fluoro salt having a formula (III), to form a poly(halotetrafluorosulfanyl)aromatic compound having a formula (IV):

$M^+F^-$ (III)

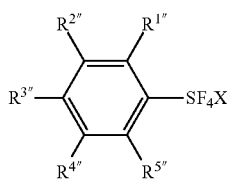

(IV)

and reacting the obtained poly(halotetrafluorosulfanyl) aromatic compound with a fluoride source to form the poly(pentafluorosulfanyl)aromatic compound;
in which: one or two of $R^1$, $R^2$, $R^3$, $R^4$, and $R^5$ are a $SF_5$ group and each of the remainders is selected from a group consisting of a hydrogen atom, a halogen atom, a substituted or unsubstituted alkyl group having 1 to 18 carbon atoms, a nitro group, and a cyano group; one or two of $R^{1'}$, $R^{2'}$, $R^{3'}$, $R^{4'}$, and $R^{5'}$ are a $SR^6$ group and each of the remainders is selected from a group consisting of a hydrogen atom, a halogen atom, a substituted or unsubstituted alkyl group having 1 to 18 carbon atoms, a nitro group, and a cyano group; one or two of $R^{1''}$, $R^{2''}$, $R^{3''}$, $R^{4''}$, and $R^{5''}$ are a $SF_4X$ group and each of the remainders is selected from a group consisting of a hydrogen atom, a halogen atom, a substituted or unsubstituted alkyl group having 1 to 18 carbon atoms, a nitro group, and a cyano group;
$R^6$ is a hydrogen atom, a silyl group, a metal atom, an ammonium moiety, a phosphonium moiety, or a halogen atom; or $R^6$ combines with another $R^6$ of its own molecule or another molecule to form a single bond;
M is a metal atom, an ammonium moiety, or a phosphonium moiety; and
X is a chlorine atom, a bromine atom, or an iodine atom.

2. The process of claim 1 wherein the halogen reacted with the aryl sulfur compound is chlorine ($Cl_2$).

3. The process of claim 1 wherein the fluoro salt having a formula (III) is an alkali metal fluoride.

4. The process of claim 1 wherein the fluoride source is at least one member selected from a group consisting of fluorides of typical elements in the Periodic Table, fluorides of transition elements in the Periodic Table, and mixture or compounds between or among these fluorides of typical elements and/or transition elements, as well as mixtures, compounds, salts, or complexes of these fluorides with fluoride source-activating compounds and/or organic molecules.

5. The process of claim 1, further comprising the reaction of the obtained poly(halotetrafluorosulfanyl)aromatic compound with a fluoride source being performed in the presence of a halogen selected from the group of chlorine, bromine, iodine, and interhalogens to form the poly(pentafluorosulfanyl)aromatic compound.

6. A process for preparing a poly(halotetrafluorosulfanyl) aromatic compound having a formula (IV):

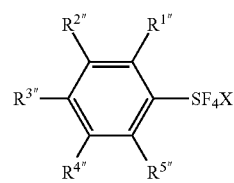

(IV)

the process comprising:
reacting an aryl sulfur compound having a formula (II):

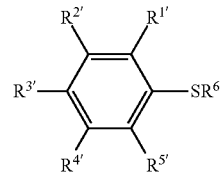

(II)

with a halogen selected from the group consisting of chlorine, bromine, iodine, and interhalogens, and a fluoro salt having a formula (III), to form the poly(halotetrafluorosulfanyl)aromatic compound, $M^+F^-$ (III)

in which: one or two of $R^{1''}$, $R^{2''}$, $R^{3''}$, $R^{4''}$, and $R^{5''}$ are a $SF_4X$ group and each of the remainders is selected from a group consisting of a hydrogen atom, a halogen atom, a substituted or unsubstituted alkyl group having 1 to 18 carbon atoms, a nitro group, and a cyano group; one or two of $R^{1'}$, $R^{2'}$, $R^{3'}$, $R^{4'}$, and $R^{5'}$ are a $SR^6$ group and each of the remainders is selected from a group consisting of a hydrogen atom, a halogen atom, a substituted or unsubstituted alkyl group having 1 to 18 carbon atoms, a nitro group, and a cyano group;
$R^6$ is a hydrogen atom, a silyl group, a metal atom, an ammonium moiety, a phosphonium moiety, or a halogen atom; or $R^6$ combines with another $R^6$ of its own molecule or another molecule to form a single bond;
M is a metal atom, an ammonium moiety, or a phosphonium moiety; and
X is a chlorine atom, a bromine atom, or an iodine atom.

7. The process of claim 6 wherein the halogen reacted with the aryl sulfur compound is chlorine ($Cl_2$).

8. The process of claim 6 wherein the fluoro salt having a formula (III) is an alkali metal fluoride.

9. A process for preparing a poly(pentafluorosulfanyl)aromatic compound having a formula (I):

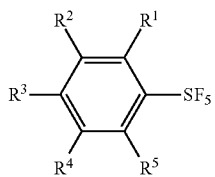

(I)

the process comprising:
reacting a poly(halotetrafluorosulfanyl)aromatic compound having a formula (IV):

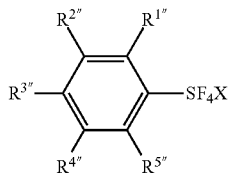

(IV)

with a fluoride source to form a poly(pentafluorosulfanyl) aromatic compound;
in which: one or two of $R^1$, $R^2$, $R^3$, $R^4$, and $R^5$ are a $SF_5$ group and each of the remainders is selected from a group consisting of a hydrogen atom, a halogen atom, a substituted or unsubstituted alkyl group having 1 to 18 carbon atoms, a nitro group, and a cyano group; one or two of $R^{1''}$, $R^{2''}$, $R^{3''}$, $R^{4''}$, and $R^{5''}$ are a $SF_4F$ group and each of the remainders is selected from a group consisting of a hydrogen atom, a halogen atom, a substituted or unsubstituted alkyl group having 1 to 18 carbon atoms, a nitro group, and a cyano group; and
X is a chlorine atom, a bromine atom, or an iodine atom.

10. The process of claim 9 wherein the fluoride source is at least one member selected from a group consisting of fluorides of typical elements in the Periodic Table, fluorides of transition elements in the Periodic Table, and mixture or compounds between or among these fluorides of typical elements and/or transition elements, as well as mixtures, compounds, salts, or complexes of these fluorides with fluoride source-activating compounds and/or organic molecules.

11. The process of claim 9 wherein X is a chlorine atom.

12. The process of claim 9, further comprising the reaction of the poly(halotetrafluorosulfanyl)aromatic compound with a fluoride source being performed in the presence of a halogen selected from the group of chlorine, bromine, iodine, and interhalogens to form the poly(pentafluorosulfanyl)aromatic compound.

* * * * *